US012715904B2

(12) United States Patent
Zhang et al.

(10) Patent No.: US 12,715,904 B2
(45) Date of Patent: Aug. 25, 2026

(54) TGF-BETA RII MUTANT AND FUSION PROTEIN THEREOF

(71) Applicant: MABWELL (SHANGHAI) BIOSCIENCE CO., LTD., Shanghai (CN)

(72) Inventors: Jinchao Zhang, Shanghai (CN); Shuang Wang, Shanghai (CN); Shasha Jiao, Shanghai (CN); Chang Zhang, Shanghai (CN); Rongjuan Wang, Shanghai (CN); Dadi Zeng, Shanghai (CN)

(73) Assignee: MABWELL (SHANGHAI) BIOSCIENCE CO., LTD., Shanghai (CN)

( * ) Notice: Subject to any disclaimer, the term of this patent is extended or adjusted under 35 U.S.C. 154(b) by 724 days.

(21) Appl. No.: 18/006,571

(22) PCT Filed: Jul. 23, 2021

(86) PCT No.: PCT/CN2021/108065
§ 371 (c)(1),
(2) Date: Jan. 23, 2023

(87) PCT Pub. No.: WO2022/017487
PCT Pub. Date: Jan. 27, 2022

(65) Prior Publication Data

US 2023/0365653 A1 Nov. 16, 2023

(30) Foreign Application Priority Data

Jul. 24, 2020 (CN) ......................... 202010721371.4

(51) Int. Cl.

| | |
|---|---|
| ***C07K 1/00*** | (2006.01) |
| ***A61P 35/00*** | (2006.01) |
| ***C07K 14/71*** | (2006.01) |
| ***C07K 16/28*** | (2006.01) |
| ***C12N 15/63*** | (2006.01) |

(52) U.S. Cl.
CPC .............. *C07K 14/71* (2013.01); *A61P 35/00* (2018.01); *C07K 16/2896* (2013.01); *C12N 15/63* (2013.01); *C07K 2317/565* (2013.01)

(58) Field of Classification Search
None
See application file for complete search history.

(56) References Cited

U.S. PATENT DOCUMENTS

2022/0017601 A1 1/2022 Tian et al.

FOREIGN PATENT DOCUMENTS

| | | | |
|---|---|---|---|
| CN | 1257545 | A | 6/2000 |
| CN | 111978412 | A | 11/2020 |
| CN | 112118858 | A | 12/2020 |
| CN | 112638374 | A | 4/2021 |
| WO | WO 98/48024 | | 10/1998 |
| WO | WO 2019/222252 | A1 | 11/2019 |
| WO | WO 2020/009992 | A1 | 1/2020 |
| WO | WO 2020/041607 | A1 | 2/2020 |
| WO | WO 2020/094122 | A1 | 5/2020 |

OTHER PUBLICATIONS

Knudson, Karin M., et al., "M7824, a novel bifunctional anti-PD-L1/TGFβ Trap fusion protein, promotes anti-tumor efficacy as monotherapy and in combination with vaccine," Oncoimmunology, 2018, vol. 7, No. 5, 14 pages.
Yaoyi Zhou et al., "Immunotherapy" "Immune checkpoint inhibitor" "Combined application", China Pharmacy, 2020, vol. 31, No. 7, pp. 890-896, http://www.cnki.net and English Abstract.

*Primary Examiner* — Chun W Dahle
(74) *Attorney, Agent, or Firm* — Lewis Roca Rothgerber Christie LLP

(57) ABSTRACT

In view of the technical problem that TGF-β RII and a fusion protein thereof are prone to degradation and breakage during the process of recombinant expression, provided are a TGF-β RII mutant and a fusion protein thereof. Compared with the extracellular region of the wild-type TGF-β RII of SEQ ID NO: 6, the TGF-β RII mutant has a mutation selected from Gln at position 6, Asp at position 12 and Gly at position 20. The TGF-β RII mutant is capable of binding to TGF-β. Compared to wild-type TGF-β RII, the TGF-β RII mutant has less breakage and/or degradation during recombination expression. It is convenient for large-scale production of antibodies/the TGF-β RII bifunctional protein with a more stable quality.

20 Claims, 15 Drawing Sheets

Specification includes a Sequence Listing.

FIG. 2b
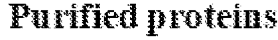
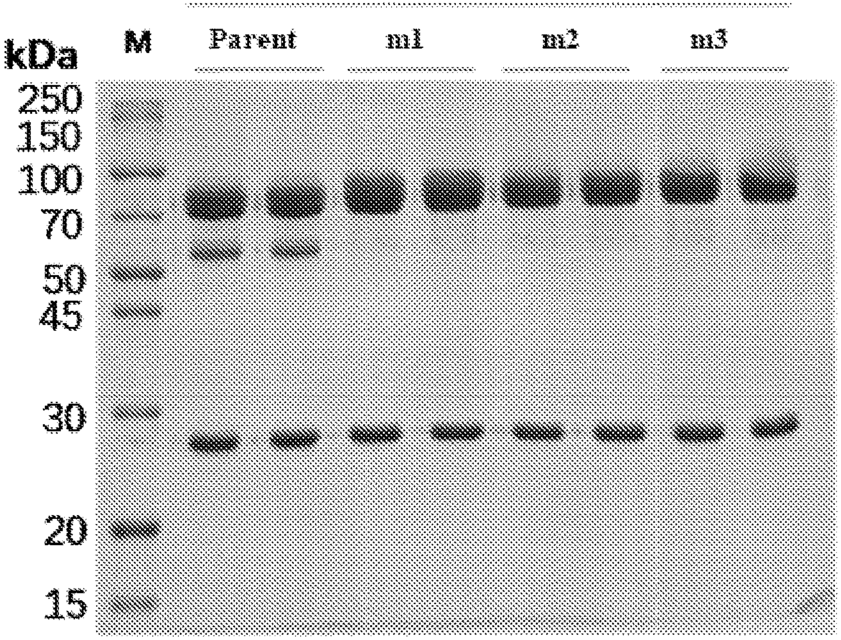
FIG. 3
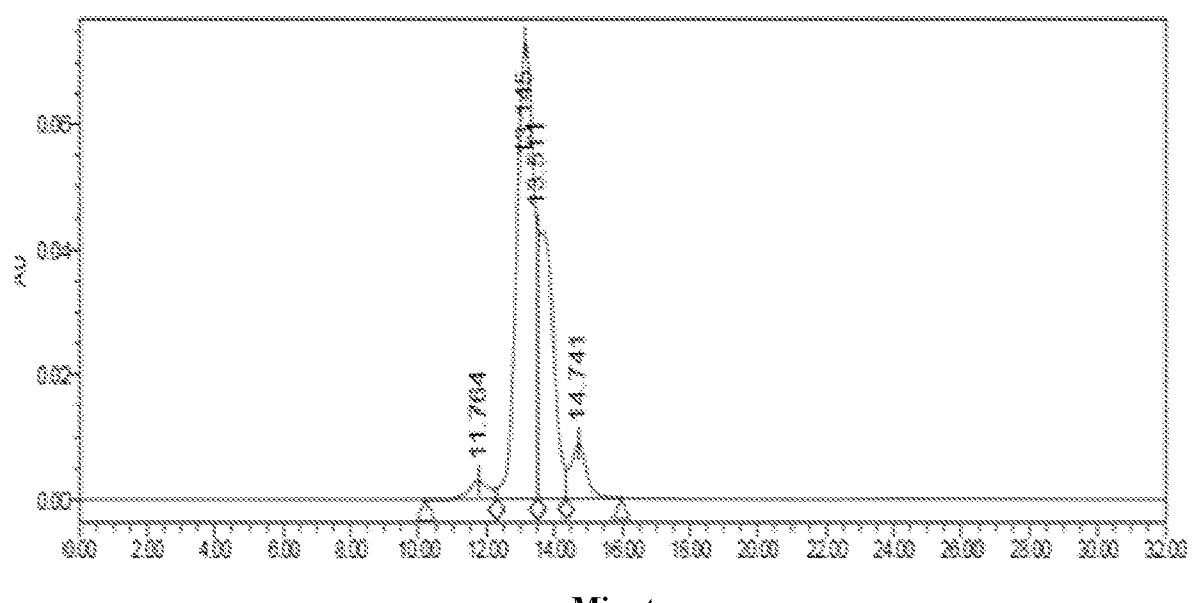

FIG. 6

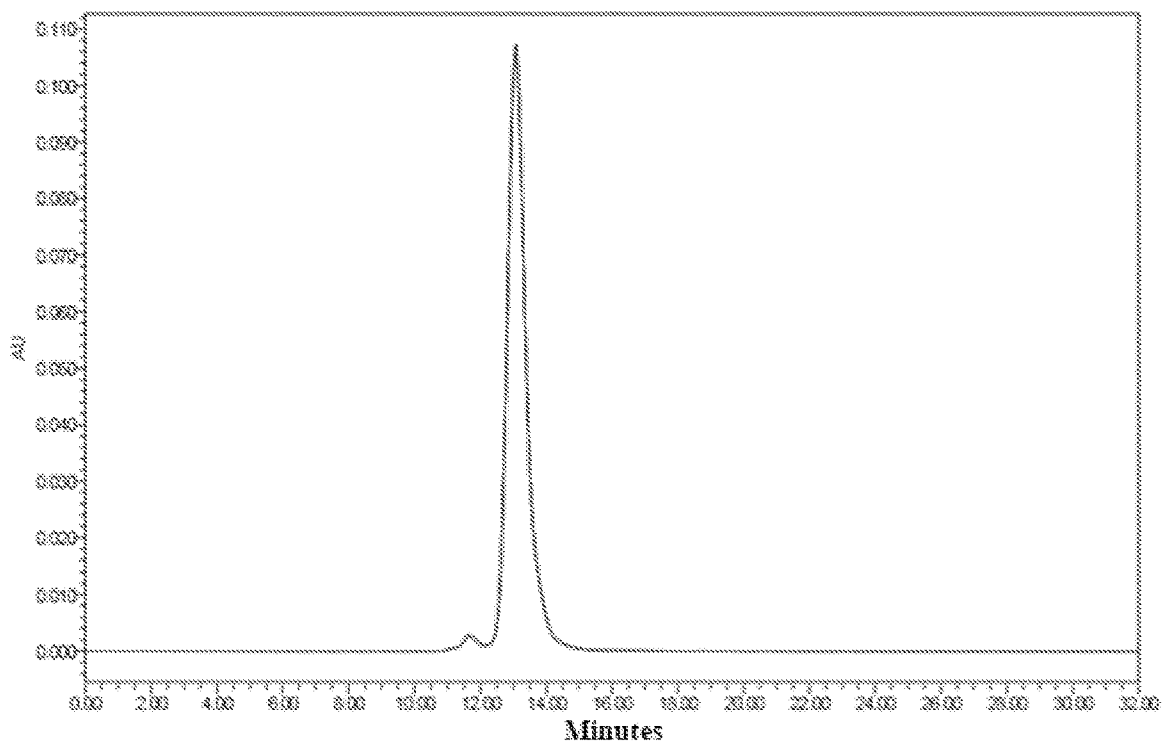

Sample name: H182-MUT4-TGF-β RIIm2-20C; Sample bottle 1: A, 5; Loading 1: Channel W2489 ChA; Collection date: 2020/2/16 14:09:02 CST Sample name: H182-MUT4-TGF-β RIIm2-freezed and thawed once; Sample bottle 1: A, 6; Loading 1; Channel W2489 ChA; Collection date: 2020/2/16 14:41:57 CST Sample name: H182-MUT4-TGF-β RIIm2- freezed and thawed 2 times; Sample bottle 1: A, 7; Loading 1; Channel W2489 ChA; Collection date: 2020/2/16 15:14:52 CST Sample name: H182-MUT4-TGF-β RIIm2- freezed and thawed 3 times; Sample bottle 1: A, 8; Loading 1; Channel W2489 ChA; Collection date: 2020/2/16 15:47:48 CST

```
                    SEQUENCE LISTING

<160> NUMBER OF SEQ ID NOS: 49

<210> SEQ ID NO 1
<211> LENGTH: 1344
<212> TYPE: DNA
<213> ORGANISM: Artificial Sequence
<220> FEATURE:
<223> OTHER INFORMATION: H182-MUT4, heavy chain

<400> SEQUENCE: 1

gaggtgcagc tggtgcagtc cggagccgag gtgaagaagc ctggagccac cgtgaagatc     60

tcctgcaagg tgtccggctt caacatcaag gacatctaca tgcactgggt gcagcaggct    120

cctggcaagg gcctggagtg gatgggacgg atcgaccctg ccaacgccaa caccaagtac    180

gaccccaagt tccaggaccg ggtgaccatc accgctgaca cctccaccaa caccgcctac    240

atggagctgt cctccctgcg gtccgaggac accgctgtgt actactgcgc ctctggccag    300

ctgggacctc tgggcttcga ctactgggga cagggcacca ccgtgaccgt gtcctccgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ctccatctcg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggt                                          1344
```

```
<210> SEQ ID NO 2
<211> LENGTH: 448
<212> TYPE: PRT
<213> ORGANISM: Artificial Sequence
<220> FEATURE:
<223> OTHER INFORMATION: H182-MUT4, heavy chain

<400> SEQUENCE: 2

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Asn Ala Asn Thr Lys Tyr Asp Pro Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gln Leu Gly Pro Leu Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 3
<211> LENGTH: 66
<212> TYPE: DNA
<213> ORGANISM: Artificial Sequence
<220> FEATURE:
<223> OTHER INFORMATION: linker

<400> SEQUENCE: 3

gctggtggag gtggctccgg aggcggagga tctggaggag gtggcagcgg cggtggaggc      60

tctggt                                                                  66


<210> SEQ ID NO 4
<211> LENGTH: 22
<212> TYPE: PRT
<213> ORGANISM: Artificial Sequence
<220> FEATURE:
<223> OTHER INFORMATION: linker

<400> SEQUENCE: 4

Ala Gly Gly Gly Gly Ser Gly Gly Gly Gly Ser Gly Gly Gly Gly Ser
1               5                   10                  15

Gly Gly Gly Gly Ser Gly
            20


<210> SEQ ID NO 5
<211> LENGTH: 408
<212> TYPE: DNA
<213> ORGANISM: Artificial Sequence
<220> FEATURE:
<223> OTHER INFORMATION: TGF-beta RII, extracellular domain

<400> SEQUENCE: 5

atccctccac acgtgcagaa gtccgtgaac aacgacatga tcgtgaccga caacaacgga      60

gccgtgaagt tccctcagct gtgcaagttc tgcgacgtgc ggttctccac ctgcgacaac     120

cagaagtcct gcatgtccaa ctgctccatc acctccatct gcgagaagcc tcaggaggtg     180

tgcgtggccg tgtggcggaa gaacgacgag aacatcaccc tggagaccgt gtgccacgac     240

cctaagctgc cctaccacga cttcatcctg gaggacgctg cctctcccaa gtgcatcatg     300

aaggagaaga agaagcctgg cgagaccttc ttcatgtgct cctgctcctc cgacgagtgc     360

aacgacaaca tcatcttctc cgaggagtac aacacctcca accctgac                  408


<210> SEQ ID NO 6
<211> LENGTH: 136
<212> TYPE: PRT
<213> ORGANISM: Artificial Sequence
<220> FEATURE:
<223> OTHER INFORMATION: TGF-beta RII, extracellular domain

<400> SEQUENCE: 6
```

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135


<210> SEQ ID NO 7
<211> LENGTH: 642
<212> TYPE: DNA
<213> ORGANISM: Artificial Sequence
<220> FEATURE:
<223> OTHER INFORMATION: H182-MUT4, light chain

<400> SEQUENCE: 7

gacatccaga tgacccagtc tccctcctct ctgtctgcct ccgtgggcga cagagtgacc      60

atcacctgca gagcctccca ggacatctcc aactacctga actggtacca gcagaagcct     120

ggcaaggctc ccaagctgct gctgtactac acctccaggc tgcactccgg agtgccctct     180

cggttctctg gctccggctc tggcaccgac tacaccctga ccatctcctc cctgcagccc     240

gaggacttcg ccacctactt ctgccagcag ggcgctggac ggccctacac cttcggagga     300

ggcaccaagg tggagatcaa gcggaccgtg gcggcgccat ctgtcttcat cttcccgcca     360

tctgatgagc agttgaaatc tggtaccgct agcgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 8
<211> LENGTH: 214
<212> TYPE: PRT
<213> ORGANISM: Artificial Sequence
<220> FEATURE:
<223> OTHER INFORMATION: H182-MUT4, light chain

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Leu
        35                  40                  45
```

```
Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ala Gly Arg Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 1818
<212> TYPE: DNA
<213> ORGANISM: Artificial Sequence
<220> FEATURE:
<223> OTHER INFORMATION: H182-MUT4-H-TGF-beta RII

<400> SEQUENCE: 9

```
gaggtgcagc tggtgcagtc cggagccgag gtgaagaagc ctggagccac cgtgaagatc     60

tcctgcaagg tgtccggctt caacatcaag gacatctaca tgcactgggt gcagcaggct    120

cctggcaagg gcctggagtg gatgggacgg atcgaccctg ccaacgccaa caccaagtac    180

gaccccaagt tccaggaccg ggtgaccatc accgctgaca cctccaccaa caccgcctac    240

atggagctgt cctccctgcg gtccgaggac accgctgtgt actactgcgc ctctggccag    300

ctgggacctc tgggcttcga ctactgggga cagggcacca ccgtgaccgt gtcctccgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ctccatctcg ggatgagctg   1080
```

```
accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtgctggt ggaggtggct ccggaggcgg aggatctgga   1380

ggaggtggca gcggcggtgg aggctctggt atccctccac acgtgcagaa gtccgtgaac   1440

aacgacatga tcgtgaccga caacaacgga gccgtgaagt tccctcagct gtgcaagttc   1500

tgcgacgtgc ggttctccac ctgcgacaac cagaagtcct gcatgtccaa ctgctccatc   1560

acctccatct gcgagaagcc tcaggaggtg tgcgtggccg tgtggcggaa gaacgacgag   1620

aacatcaccc tggagaccgt gtgccacgac cctaagctgc cctaccacga cttcatcctg   1680

gaggacgctg cctctcccaa gtgcatcatg aaggagaaga agaagcctgg cgagaccttc   1740

ttcatgtgct cctgctcctc cgacgagtgc aacgacaaca tcatcttctc cgaggagtac   1800

aacacctcca accctgac                                                 1818
```

```
<210> SEQ ID NO 10
<211> LENGTH: 606
<212> TYPE: PRT
<213> ORGANISM: Artificial Sequence
<220> FEATURE:
<223> OTHER INFORMATION: H182-MUT4-H-TGF-beta RII

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Asn Ala Asn Thr Lys Tyr Asp Pro Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gln Leu Gly Pro Leu Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Gly Ile Pro Pro His Val Gln Lys Ser Val Asn
465                 470                 475                 480

Asn Asp Met Ile Val Thr Asp Asn Asn Gly Ala Val Lys Phe Pro Gln
                485                 490                 495

Leu Cys Lys Phe Cys Asp Val Arg Phe Ser Thr Cys Asp Asn Gln Lys
            500                 505                 510

Ser Cys Met Ser Asn Cys Ser Ile Thr Ser Ile Cys Glu Lys Pro Gln
        515                 520                 525

Glu Val Cys Val Ala Val Trp Arg Lys Asn Asp Glu Asn Ile Thr Leu
    530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
                565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605
```

<210> SEQ ID NO 11
<211> LENGTH: 1818
<212> TYPE: DNA
<213> ORGANISM: Artificial Sequence
<220> FEATURE:
<223> OTHER INFORMATION: H182-MUT4-H-TGF-beta RII m1

<400> SEQUENCE: 11

```
gaggtgcagc tggtgcagtc cggagccgag gtgaagaagc ctggagccac cgtgaagatc      60
tcctgcaagg tgtccggctt caacatcaag gacatctaca tgcactgggt gcagcaggct     120
cctggcaagg gcctggagtg gatgggacgg atcgaccctg ccaacgccaa caccaagtac     180
gaccccaagt tccaggaccg ggtgaccatc accgctgaca cctccaccaa caccgcctac     240
atggagctgt cctccctgcg gtccgaggac accgctgtgt actactgcgc ctctggccag     300
ctgggacctc tgggcttcga ctactgggga cagggcacca ccgtgaccgt gtcctccgct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ctccatctcg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtgctggt ggaggtggct ccggaggcgg aggatctgga    1380
ggaggtggca gcggcggtgg aggctctggt atccctccac acgtgcagaa gtccgtgaac    1440
aacgacatga tcgtgaccga caacaacacc gccgtgaagt tccctcagct gtgcaagttc    1500
tgcgacgtgc ggttctccac ctgcgacaac cagaagtcct gcatgtccaa ctgctccatc    1560
acctccatct gcgagaagcc tcaggaggtg tgcgtggccg tgtggcggaa gaacgacgag    1620
aacatcaccc tggagaccgt gtgccacgac cctaagctgc cctaccacga cttcatcctg    1680
gaggacgctg cctctcccaa gtgcatcatg aaggagaaga agaagcctgg cgagaccttc    1740
ttcatgtgct cctgctcctc cgacgagtgc aacgacaaca tcatcttctc cgaggagtac    1800
aacacctcca accctgac                                                  1818
```

<210> SEQ ID NO 12
<211> LENGTH: 606
<212> TYPE: PRT
<213> ORGANISM: Artificial Sequence
<220> FEATURE:
<223> OTHER INFORMATION: H182-MUT4-H-TGF-beta RII m1

<400> SEQUENCE: 12

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30
```

```
Tyr Met His Trp Val Gln Gln Ala Pro Gly Lys Gly Leu Glu Trp Met
        35                  40                  45

Gly Arg Ile Asp Pro Ala Asn Ala Asn Thr Lys Tyr Asp Pro Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gln Leu Gly Pro Leu Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

```
Ala Gly Gly Gly Gly Ser Gly Gly Gly Gly Ser Gly Gly Gly Gly Ser
    450                 455                 460

Gly Gly Gly Gly Ser Gly Ile Pro Pro His Val Gln Lys Ser Val Asn
465                 470                 475                 480

Asn Asp Met Ile Val Thr Asp Asn Asn Thr Ala Val Lys Phe Pro Gln
                485                 490                 495

Leu Cys Lys Phe Cys Asp Val Arg Phe Ser Thr Cys Asp Asn Gln Lys
            500                 505                 510

Ser Cys Met Ser Asn Cys Ser Ile Thr Ser Ile Cys Glu Lys Pro Gln
        515                 520                 525

Glu Val Cys Val Ala Val Trp Arg Lys Asn Asp Glu Asn Ile Thr Leu
    530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
                565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605
```

<210> SEQ ID NO 13
<211> LENGTH: 1818
<212> TYPE: DNA
<213> ORGANISM: Artificial Sequence
<220> FEATURE:
<223> OTHER INFORMATION: H182-MUT4-H-TGF-beta RII m2

<400> SEQUENCE: 13

```
gaggtgcagc tggtgcagtc cggagccgag gtgaagaagc ctggagccac cgtgaagatc     60

tcctgcaagg tgtccggctt caacatcaag gacatctaca tgcactgggt gcagcaggct    120

cctggcaagg gcctggagtg gatgggacgg atcgaccctg ccaacgccaa caccaagtac    180

gaccccaagt tccaggaccg ggtgaccatc accgctgaca cctccaccaa caccgcctac    240

atggagctgt cctccctgcg gtccgaggac accgctgtgt actactgcgc ctctggccag    300

ctgggacctc tgggcttcga ctactgggga cagggcacca ccgtgaccgt gtcctccgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ctccatctcg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200
```

```
gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtgctggt ggaggtggct ccggaggcgg aggatctgga   1380

ggaggtggca gcggcggtgg aggctctggt atccctccac acgtgaacaa gtccgtgaac   1440

aacgacatga tcgtgaccga caacaacgga gccgtgaagt tccctcagct gtgcaagttc   1500

tgcgacgtgc ggttctccac ctgcgacaac cagaagtcct gcatgtccaa ctgctccatc   1560

acctccatct gcgagaagcc tcaggaggtg tgcgtggccg tgtggcggaa gaacgacgag   1620

aacatcaccc tggagaccgt gtgccacgac cctaagctgc cctaccacga cttcatcctg   1680

gaggacgctg cctctcccaa gtgcatcatg aaggagaaga agaagcctgg cgagaccttc   1740

ttcatgtgct cctgctcctc cgacgagtgc aacgacaaca tcatcttctc cgaggagtac   1800

aacacctcca accctgac                                                 1818
```

<210> SEQ ID NO 14
<211> LENGTH: 606
<212> TYPE: PRT
<213> ORGANISM: Artificial Sequence
<220> FEATURE:
<223> OTHER INFORMATION: H182-MUT4-H-TGF-beta RII m2

<400> SEQUENCE: 14

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Asn Ala Asn Thr Lys Tyr Asp Pro Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gln Leu Gly Pro Leu Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Gly Ile Pro Pro His Val Asn Lys Ser Val Asn
465                 470                 475                 480

Asn Asp Met Ile Val Thr Asp Asn Asn Gly Ala Val Lys Phe Pro Gln
                485                 490                 495

Leu Cys Lys Phe Cys Asp Val Arg Phe Ser Thr Cys Asp Asn Gln Lys
            500                 505                 510

Ser Cys Met Ser Asn Cys Ser Ile Thr Ser Ile Cys Glu Lys Pro Gln
        515                 520                 525

Glu Val Cys Val Ala Val Trp Arg Lys Asn Asp Glu Asn Ile Thr Leu
    530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
                565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605


<210> SEQ ID NO 15
<211> LENGTH: 1818
<212> TYPE: DNA
<213> ORGANISM: Artificial Sequence
<220> FEATURE:
<223> OTHER INFORMATION: H182-MUT4-H-TGF-beta RII m3

<400> SEQUENCE: 15

gaggtgcagc tggtgcagtc cggagccgag gtgaagaagc ctggagccac cgtgaagatc      60
```

```
tcctgcaagg tgtccggctt caacatcaag gacatctaca tgcactgggt gcagcaggct    120
cctggcaagg gcctggagtg gatgggacgg atcgaccctg ccaacgccaa caccaagtac    180
gaccccaagt tccaggaccg ggtgaccatc accgctgaca cctccaccaa caccgcctac    240
atggagctgt cctccctgcg gtccgaggac accgctgtgt actactgcgc ctctggccag    300
ctgggacctc tgggcttcga ctactgggga cagggcacca ccgtgaccgt gtcctccgct    360
agcaccaagg gcccatcggt cttcccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ctccatctcg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggtgctggt ggaggtggct ccggaggcgg aggatctgga   1380
ggaggtggca gcggcggtgg aggctctggt atccctccac acgtgcagaa gtccgtgaac   1440
aacaccatga tcgtgaccga caacaacgga gccgtgaagt tccctcagct gtgcaagttc   1500
tgcgacgtgc ggttctccac ctgcgacaac cagaagtcct gcatgtccaa ctgctccatc   1560
acctccatct gcgagaagcc tcaggaggtg tgcgtggccg tgtggcggaa gaacgacgag   1620
aacatcaccc tggagaccgt gtgccacgac cctaagctgc cctaccacga cttcatcctg   1680
gaggacgctg cctctcccaa gtgcatcatg aaggagaaga agaagcctgg cgagaccttc   1740
ttcatgtgct cctgctcctc cgacgagtgc aacgacaaca tcatcttctc cgaggagtac   1800
aacacctcca accctgac                                                 1818
```

```
<210> SEQ ID NO 16
<211> LENGTH: 606
<212> TYPE: PRT
<213> ORGANISM: Artificial Sequence
<220> FEATURE:
<223> OTHER INFORMATION: H182-MUT4-H-TGF-beta RII m3

<400> SEQUENCE: 16

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45
```

```
Gly Arg Ile Asp Pro Ala Asn Ala Asn Thr Lys Tyr Asp Pro Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gln Leu Gly Pro Leu Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460
```

```
Gly Gly Gly Gly Ser Gly Ile Pro Pro His Val Gln Lys Ser Val Asn
465                 470                 475                 480

Asn Thr Met Ile Val Thr Asp Asn Asn Gly Ala Val Lys Phe Pro Gln
                485                 490                 495

Leu Cys Lys Phe Cys Asp Val Arg Phe Ser Thr Cys Asp Asn Gln Lys
            500                 505                 510

Ser Cys Met Ser Asn Cys Ser Ile Thr Ser Ile Cys Glu Lys Pro Gln
        515                 520                 525

Glu Val Cys Val Ala Val Trp Arg Lys Asn Asp Glu Asn Ile Thr Leu
    530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
                565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605


<210> SEQ ID NO 17
<211> LENGTH: 216
<212> TYPE: PRT
<213> ORGANISM: Artificial Sequence
<220> FEATURE:
<223> OTHER INFORMATION: M7824, light chain

<400> SEQUENCE: 17

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 18
<211> LENGTH: 607
<212> TYPE: PRT
<213> ORGANISM: Artificial Sequence
<220> FEATURE:
<223> OTHER INFORMATION: M7824 heavy chain-TGF-beta RII

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

-continued

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ala Gly Gly Gly Gly Ser Gly Gly Gly Gly Ser Gly Gly Gly Gly
    450                 455                 460

Ser Gly Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
        515                 520                 525

Gln Glu Val Cys Val Ala Val Trp Arg Lys Asn Asp Glu Asn Ile Thr
    530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys Lys
                565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605


<210> SEQ ID NO 19
<211> LENGTH: 1059
<212> TYPE: DNA
<213> ORGANISM: Artificial Sequence
<220> FEATURE:
<223> OTHER INFORMATION: hzF2

<400> SEQUENCE: 19

gaggtgcagc tggtggagtc tggaggtggc ctggtgcagc ctggaggctc cctgaggctg      60

tcctgcgctg cctctcggga ctccgacgag ggagcctcct gcatgggctg gttcaggcag     120

gctcctggca aggagagaga gggagtggcc atcatcttca acgctggcga gcggaccgac     180

tacggcgact ccgtgaaggg acggttcacc atctccaggg acaacgccaa gaacaccctg     240

tacctgcaga tgaactccct gagagccgag gacacagccg tgtactactg cgctaccgtg     300

tggtgtggct cctgggtggc tcggtcctgg ggacagggca ccctggtgac cgtgtcctcc     360

gctagcgagc ccaaatctag cgacaaaact cacacatgcc caccgtgccc agcacctgaa     420

ctcctggggg gaccgtcagt cttcctcttc cccccaaaac ccaaggacac cctcatgatc     480

tcccggaccc ctgaggtcac atgcgtggtg gtggacgtga gccacgaaga ccctgaggtc     540

aagttcaact ggtacgtgga cggcgtggag gtgcataatg ccaagacaaa gccgcgggag     600

gagcagtaca acagcacgta ccgtgtggtc agcgtcctca ccgtcctgca ccaggactgg     660

ctgaatggca aggagtacaa gtgcaaggtc tccaacaaag ccctcccagc ccccatcgag     720
```

```
aaaaccatct ccaaagccaa agggcagccc cgagaaccac aggtgtacac cctgcctcca    780

tctcgggatg agctgaccaa gaaccaggtc agcctgacct gcctggtcaa aggcttctat    840

cccagcgaca tcgccgtgga gtgggagagc aatgggcagc cggagaacaa ctacaagacc    900

acgcctcccg tgctggactc cgacggctcc ttcttcctct atagcaagct caccgtggac    960

aagagcaggt ggcagcaggg gaacgtcttc tcatgctccg tgatgcatga ggctctgcac   1020

aaccactaca cgcagaagag cctctccctg tccccgggt                          1059
```

```
<210> SEQ ID NO 20
<211> LENGTH: 353
<212> TYPE: PRT
<213> ORGANISM: Artificial Sequence
<220> FEATURE:
<223> OTHER INFORMATION: hzF2

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Arg Asp Ser Asp Glu Gly Ala
            20                  25                  30

Ser Cys Met Gly Trp Phe Arg Gln Ala Pro Gly Lys Glu Arg Glu Gly
        35                  40                  45

Val Ala Ile Ile Phe Asn Ala Gly Glu Arg Thr Asp Tyr Gly Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Thr Val Trp Cys Gly Ser Trp Val Ala Arg Ser Trp Gly Gln
            100                 105                 110

Gly Thr Leu Val Thr Val Ser Ser Ala Ser Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300
```

```
Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly


<210> SEQ ID NO 21
<211> LENGTH: 63
<212> TYPE: DNA
<213> ORGANISM: Artificial Sequence
<220> FEATURE:
<223> OTHER INFORMATION: linker

<400> SEQUENCE: 21

ggtggaggtg gctccggagg cggaggatct ggaggaggtg gcagcggcgg tggaggctct     60

ggt                                                                   63


<210> SEQ ID NO 22
<211> LENGTH: 21
<212> TYPE: PRT
<213> ORGANISM: Artificial Sequence
<220> FEATURE:
<223> OTHER INFORMATION: linker

<400> SEQUENCE: 22

Gly Gly Gly Gly Ser Gly Gly Gly Gly Ser Gly Gly Gly Gly Ser Gly
1               5                   10                  15

Gly Gly Gly Ser Gly
            20


<210> SEQ ID NO 23
<211> LENGTH: 1530
<212> TYPE: DNA
<213> ORGANISM: Artificial Sequence
<220> FEATURE:
<223> OTHER INFORMATION: hzF2-TGF-beta RIIm2

<400> SEQUENCE: 23

gaggtgcagc tggtggagtc tggaggtggc ctggtgcagc ctggaggctc cctgaggctg     60

tcctgcgctg cctctcggga ctccgacgag ggagcctcct gcatgggctg gttcaggcag    120

gctcctggca aggagagaga gggagtggcc atcatcttca acgctggcga gcggaccgac    180

tacggcgact ccgtgaaggg acggttcacc atctccaggg acaacgccaa gaacaccctg    240

tacctgcaga tgaactccct gagagccgag gacacagccg tgtactactg cgctaccgtg    300

tggtgtggct cctgggtggc tcggtcctgg ggacagggca ccctggtgac cgtgtcctcc    360

gctagcgagc ccaaatctag cgacaaaact cacacatgcc caccgtgccc agcacctgaa    420

ctcctggggg gaccgtcagt cttcctcttc cccccaaaac ccaaggacac cctcatgatc    480

tcccggaccc ctgaggtcac atgcgtggtg gtggacgtga gccacgaaga ccctgaggtc    540

aagttcaact ggtacgtgga cggcgtggag gtgcataatg ccaagacaaa gccgcgggag    600

gagcagtaca acagcacgta ccgtgtggtc agcgtcctca ccgtcctgca ccaggactgg    660

ctgaatggca aggagtacaa gtgcaaggtc tccaacaaag ccctcccagc ccccatcgag    720

aaaaccatct ccaaagccaa agggcagccc cgagaaccac aggtgtacac cctgcctcca    780

tctcgggatg agctgaccaa gaaccaggtc agcctgacct gcctggtcaa aggcttctat    840
```

-continued

```
cccagcgaca tcgccgtgga gtgggagagc aatgggcagc cggagaacaa ctacaagacc    900

acgcctcccg tgctggactc cgacggctcc ttcttcctct atagcaagct caccgtggac    960

aagagcaggt ggcagcaggg gaacgtcttc tcatgctccg tgatgcatga ggctctgcac   1020

aaccactaca cgcagaagag cctctccctg tccccgggtg gtggaggtgg ctccggaggc   1080

ggaggatctg gaggaggtgg cagcggcggt ggaggctctg gtatccctcc acacgtgaac   1140

aagtccgtga acaacgacat gatcgtgacc gacaacaacg gagccgtgaa gttccctcag   1200

ctgtgcaagt tctgcgacgt gcggttctcc acctgcgaca accagaagtc ctgcatgtcc   1260

aactgctcca tcacctccat ctgcgagaag cctcaggagg tgtgcgtggc cgtgtggcgg   1320

aagaacgacg agaacatcac cctggagacc gtgtgccacg accctaagct gccctaccac   1380

gacttcatcc tggaggacgc tgcctctccc aagtgcatca tgaaggagaa gaagaagcct   1440

ggcgagacct tcttcatgtg ctcctgctcc tccgacgagt gcaacgacaa catcatcttc   1500

tccgaggagt acaacacctc caaccctgac                                    1530
```

```
<210> SEQ ID NO 24
<211> LENGTH: 510
<212> TYPE: PRT
<213> ORGANISM: Artificial Sequence
<220> FEATURE:
<223> OTHER INFORMATION: hzF2-TGF-beta RIIm2

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Arg Asp Ser Asp Glu Gly Ala
            20                  25                  30

Ser Cys Met Gly Trp Phe Arg Gln Ala Pro Gly Lys Glu Arg Glu Gly
        35                  40                  45

Val Ala Ile Ile Phe Asn Ala Gly Glu Arg Thr Asp Tyr Gly Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Thr Val Trp Cys Gly Ser Trp Val Ala Arg Ser Trp Gly Gln
            100                 105                 110

Gly Thr Leu Val Thr Val Ser Ser Ala Ser Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240
```

```
Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Gly Gly Gly Gly Ser Gly Gly Gly Gly Ser Gly Gly Gly Gly Ser
        355                 360                 365

Gly Gly Gly Gly Ser Gly Ile Pro Pro His Val Asn Lys Ser Val Asn
    370                 375                 380

Asn Asp Met Ile Val Thr Asp Asn Asn Gly Ala Val Lys Phe Pro Gln
385                 390                 395                 400

Leu Cys Lys Phe Cys Asp Val Arg Phe Ser Thr Cys Asp Asn Gln Lys
                405                 410                 415

Ser Cys Met Ser Asn Cys Ser Ile Thr Ser Ile Cys Glu Lys Pro Gln
            420                 425                 430

Glu Val Cys Val Ala Val Trp Arg Lys Asn Asp Glu Asn Ile Thr Leu
        435                 440                 445

Glu Thr Val Cys His Asp Pro Lys Leu Pro Tyr His Asp Phe Ile Leu
    450                 455                 460

Glu Asp Ala Ala Ser Pro Lys Cys Ile Met Lys Glu Lys Lys Lys Pro
465                 470                 475                 480

Gly Glu Thr Phe Phe Met Cys Ser Cys Ser Ser Asp Glu Cys Asn Asp
                485                 490                 495

Asn Ile Ile Phe Ser Glu Glu Tyr Asn Thr Ser Asn Pro Asp
            500                 505                 510
```

<210> SEQ ID NO 25
<211> LENGTH: 5
<212> TYPE: PRT
<213> ORGANISM: Artificial Sequence
<220> FEATURE:
<223> OTHER INFORMATION: H182-MUT4, heavy chain CDR1

<400> SEQUENCE: 25

```
Asp Ile Tyr Met His
1               5
```

<210> SEQ ID NO 26
<211> LENGTH: 17
<212> TYPE: PRT
<213> ORGANISM: Artificial Sequence
<220> FEATURE:
<223> OTHER INFORMATION: H182-MUT4, heavy chain CDR2

<400> SEQUENCE: 26

```
Arg Ile Asp Pro Ala Asn Ala Asn Thr Lys Tyr Asp Pro Lys Phe Gln
1               5                   10                  15

Asp
```

<210> SEQ ID NO 27
<211> LENGTH: 10
<212> TYPE: PRT
<213> ORGANISM: Artificial Sequence
<220> FEATURE:
<223> OTHER INFORMATION: H182-MUT4, heavy chain CDR3

<400> SEQUENCE: 27

```
Gly Gln Leu Gly Pro Leu Gly Phe Asp Tyr
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: H182-MUT4, light chain CDR1

<400> SEQUENCE: 28

```
Arg Ala Ser Gln Asp Ile Ser Asn Tyr Leu Asn
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: H182-MUT4, light chain CDR2

<400> SEQUENCE: 29

```
Tyr Thr Ser Arg Leu His Ser
1               5
```

<210> SEQ ID NO 30
<211> LENGTH: 9
<212> TYPE: PRT
<213> ORGANISM: Artificial Sequence
<220> FEATURE:
<223> OTHER INFORMATION: H182-MUT4, light chain CDR3

<400> SEQUENCE: 30

```
Gln Gln Gly Ala Gly Arg Pro Tyr Thr
1               5
```

<210> SEQ ID NO 31
<211> LENGTH: 16
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 31

```
Val Val Ser Val Leu Thr Val Leu His Gln Asp Trp Leu Asn Gly Lys
1               5                   10                  15
```

<210> SEQ ID NO 32
<211> LENGTH: 23
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 32

```
Trp Gln Gln Gly Asn Val Phe Ser Cys Ser Val Met His Glu Ala Leu
1               5                   10                  15

His Asn His Tyr Thr Gln Lys
```

20

<210> SEQ ID NO 33
<211> LENGTH: 10
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 33

Asn Gln Val Ser Leu Thr Cys Leu Val Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 34

Phe Asn Trp Tyr Val Asp Gly Val Glu Val His Asn Ala Lys
1               5                   10

<210> SEQ ID NO 35
<211> LENGTH: 7
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 35

Asp Thr Leu Met Ile Ser Arg
1               5

<210> SEQ ID NO 36
<211> LENGTH: 12
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 36

Gly Pro Ser Val Phe Pro Leu Ala Pro Ser Ser Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 37

Glu Val Gln Leu Val Gln Ser Gly Ala Glu Val Lys
1               5                   10

<210> SEQ ID NO 38
<211> LENGTH: 20
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 38

Val Thr Ile Thr Ala Asp Thr Ser Thr Asn Thr Ala Tyr Met Glu Leu
1               5                   10                  15

```
Ser Ser Leu Arg
            20


<210> SEQ ID NO 39
<211> LENGTH: 13
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 39

Asp Ile Tyr Met His Trp Val Gln Gln Ala Pro Gly Lys
1               5                   10


<210> SEQ ID NO 40
<211> LENGTH: 11
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 40

Glu Pro Gln Val Tyr Thr Leu Pro Pro Ser Arg
1               5                   10


<210> SEQ ID NO 41
<211> LENGTH: 7
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 41

Gly Leu Glu Trp Met Gly Arg
1               5


<210> SEQ ID NO 42
<211> LENGTH: 8
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 42

Ala Leu Pro Ala Pro Ile Glu Lys
1               5


<210> SEQ ID NO 43
<211> LENGTH: 26
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 43

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25


<210> SEQ ID NO 44
<211> LENGTH: 22
<212> TYPE: PRT
<213> ORGANISM: Artificial Sequence
<220> FEATURE:
<223> OTHER INFORMATION: fragment derived from H182-MUT4-H-TGF-beta RII
```

<400> SEQUENCE: 44

Gly Phe Tyr Pro Ser Asp Ile Ala Val Glu Trp Glu Ser Asn Gly Gln
1 5 10 15

Pro Glu Asn Asn Tyr Lys
20

<210> SEQ ID NO 45
<211> LENGTH: 16
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 45

Glu Pro Gln Val Tyr Thr Leu Pro Pro Ser Arg Asp Glu Leu Thr Lys
1 5 10 15

<210> SEQ ID NO 46
<211> LENGTH: 17
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 46

Thr Thr Pro Pro Val Leu Asp Ser Asp Gly Ser Phe Phe Leu Tyr Ser
1 5 10 15

Lys

<210> SEQ ID NO 47
<211> LENGTH: 9
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 47

Ile Asp Pro Ala Asn Ala Asn Thr Lys
1 5

<210> SEQ ID NO 48
<211> LENGTH: 36
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 48

Ser Leu Ser Leu Ser Pro Gly Ala Gly Gly Gly Gly Ser Gly Gly Gly
1 5 10 15

Gly Ser Gly Gly Gly Gly Ser Gly Gly Gly Gly Ser Gly Ile Pro Pro
20 25 30

His Val Gln Lys
35

-continued

```
<210> SEQ ID NO 49
<211> LENGTH: 30
<212> TYPE: PRT
<213> ORGANISM: Artificial Sequence
<220> FEATURE:
<223> OTHER INFORMATION: fragment derived from H182-MUT4-H-TGF-beta RII

<400> SEQUENCE: 49

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30
```

TGF-BETA RII MUTANT AND FUSION PROTEIN THEREOF

CROSS-REFERENCE TO RELATED APPLICATION(S)

The present patent application is a U.S. National Phase Patent Application of International Application Number PCT/CN2021/108065, filed on Jul. 23, 2021, which claims the benefit of priority of the Chinese Patent Application Number 202010721371.4 filed on Jul. 24, 2020, the entire content of each of which is incorporated herein by reference.

SEQUENCE LISTING

The instant application contains a Sequence Listing in ASCII format Version 2.1 via EFS-web, and the entire content of the electronic submission of the sequence listing is incorporated by reference in its entirety for all purposes. The ASCII text file is named "233685_revised_sequence_listing.txt," was created on Jul. 21, 2023, and is 66,634 bytes in size.

TECHNICAL FIELD

The invention belongs to the field of biological pharmacy, in particular to the field of therapeutic protein medicines for tumor. Specifically, the invention relates to a TGF-β RII mutant and a fusion protein and applications thereof.

BACKGROUND OF THE INVENTION

Programmed death factor ligand 1 (PD-L1), also known as cluster of differentiation 274 (CD274) or B7 homologous protein 1 (B7-H1), is a member of the B7 family and is encoded by the CD274 gene. The mature PD-L1 protein has a size of 40 kDa, is a type I transmembrane protein consisting of 272 amino acids, and is inducibly expressed on the surface of activated T cells, B cells, dendritic cells, macrophages, mesenchymal stem cells, bone marrow-derived mast cells and non-hematopoietic cells; and is also widely expressed on tumor tissues, e.g., lung cancer, liver cancer, bladder cancer, and the like. The expression of PD-L1 may be rapidly up-regulated in tumor tissues and other tissues in response to the stimulation by interferons and other inflammatory factors. The receptor for PD-L1 is programmed death protein 1 (PD-1). PD-1, also known as CD279, is a member of the CD28 family of T cell receptors and is expressed on the surface of a variety of immune cells, e.g., activated T cells, B cells, monocytes, and the like. Upon PD-L1 binds to its receptor PD-1, T cell apoptosis, anergy and exhaustion can be induced, and then the activation, proliferation and anti-tumor function of tumor antigen specific T cells are inhibited, resulting in tumor immune escape. PD-1/PD-L1 blocking antibodies can relieve the immunosuppression effect of PD-L1, and enhance the recognition and killing of tumor cells by in vivo immune cells such as T cells, thereby achieving the effect of killing tumors. So far a plurality of antibody medicines targeting PD-1/PD-L1 are marketed worldwide, and show clinically good therapeutic effects on various tumors including melanoma, lung cancer, kidney cancer, Hodgkin lymphoma, head and neck squamous cell carcinoma, urothelial carcinoma and the like. However, there are still certain problems with therapeutic PD-1/PD-L1 antibodies, and the main problem is the low effective rate when such an antibody is used alone clinically. For most cancers, only an effective rate of 10%-20% on average can be achieved if a therapeutic PD-1/PD-L1 antibody is used alone indiscriminately. Therefore, it is desirable to develop more effective antibody molecules to meet clinical needs.

Transforming growth factor-β (TGF-β) is a member of the TGF-β superfamily, whose major function is to regulate cell growth and differentiation. TGF-β has high affinity receptors (TGF-β Rs) on the cell surface which are divided into 3 subtypes: TGF-β RI, TGF-β RII, and TGF-β RIII Via binding to TGF-β RII having a serine/threonine protein kinase activity on the surface of the cell membrane, TGF-β forms a complex with TGF-β RII which in turn complexed with TGF-β RI, thereby transmitting signals to cause the activation of corresponding signaling pathways and playing roles in regulating cell proliferation, differentiation and apoptosis. In a tumor microenvironment, TGF-β has the effects of regulating the development of regulatory T cells (Tregs), inhibiting the maturation of DC cells, inhibiting the generation of IgA by B cells, inhibiting the activation of NK cells, and the like, thereby resulting in immunosuppression to promote the growth and metastasis of tumor cells. Through blocking the binding of TGF-β to its major receptor TGF-β RII, the tumor-promoting activity of TGF-β can be inhibited. Therefore, the development of TGF-β blocking medicines is an important direction for tumor treatment.

At present, a number of small molecule inhibitors and macromolecular protein medicines targeting the TGF-β pathway are at clinical research stages, and a plurality of clinical trials about the combined use with PD-1/PD-L1 antibody medicines are under way; and the mechanism of the combined use has been deeply explored, as reported in literatures (Nature, 2018 Feb. 22. doi: 10.1038/nature 25492; Nature, 2018 Feb. 22. doi: 10.1038/nature 25501). Therefore, the development of a therapy or a medicament capable of blocking both PD-1/PD-L1 and TGF-β/TGF-β-R pathways, is expected to further solve the problem of the immunosuppression in tumor microenvironments.

Based on the combined use of TGF-β blocker and PD-1/PD-L1 inhibitor, a medicine which simultaneously blocks both PD-1/PD-L1 and TGF-β/TGF-β-R pathways has been further developed. Clinical data of the bifunctional fusion protein M7824 formed by a PD-L1 antibody and TGF-β RII from Merck & GSK show that it has definite clinical therapeutic effects on a variety of solid tumors (NCT02699515, NCT02517398, and NCT03427411). A number of patent applications have been filed by Merck for the structure of M7824, see WO2015118175A2. Certain bifunctional molecules of similar structure enter into clinical trials successively, for example, SHR-1701 developed by Hengrui Medicine (CTR20182404\CTR20181823). Now many antibody/TGF-β RII fusion proteins are disclosed in patent documents such as WO2006074451A2, WO2009152610A1, WO9309228A1, WO9409815A1 and WO2015118175A2 etc., but some of the fusion proteins have the problem of being unstable. In actual production and application, there is still a need to develop antibody/TGF-β R fusion proteins which are more stable and highly expressed.

Although M7824 has a good anti-tumor effect, a problem that it is easy to break at TGF-β RII exists in production, which brings some difficulties to the processing and quality control during its production. To solve the problem, Hengrui Medicine designed a truncated form of TGF-β RII; the study shown in the patent document WO2018/205985A1 found, a truncated form comprising a deletion of the first 26 amino acids, especially a deletion of amino acids at positions 14-21 at the N-terminus of TGF-β RII maintains physiological functions of TGF-β MI and is more stable. However, the TGF-β RII comprised in an antibody/TGF-β MI fusion protein is smaller than the antibody, so the function of TGF-β RII in the fusion protein is susceptible to interference from the antibody molecule, even is shielded by the antibody molecule. Such a problem can only be alleviated to a certain extent even with a flexible linker; while the truncation at the N-terminus of TGF-β MI would further exacerbate the difference in molecule size between the two functional parts of an antibody/TGF-β RII fusion protein molecule.

SUMMARY OF THE INVENTION

The technical problem to be solved by the invention is: antibody/TGF-β MI fusion proteins in prior arts are susceptible to breakage and degradation during production, and the difference in molecule size between the two functional parts of the antibody/TGF-β RII fusion proteins will be further aggravated if an N-terminally truncated TGF-β MI is used.

The inventors discovered from research that the main reason behind the instability of an antibody/TGF-β MI fusion protein is as follows: after the C terminus of the antibody is linked to TGF-β MI via a linker peptide, a breakage may occur between the antibody and the TGF-β MI and lead to an incomplete structure of the fusion protein, thereby affecting the purity and the quality uniformity of the fusion protein, and in turn causing medicine safety and effectiveness concerns. On the basis of that finding, a technical solution for performing mutation modification on TGF-β MI is provided herein, which can overcome the defect of being susceptible to breakage and degradation of the antibody/TGF-β RII fusion protein and also balance the molecule sizes of the two functional parts, to provide an antibody/TGF-β RII fusion protein which is more convenient for large-scale production with more stable quality. Specifically, technical solutions of the invention are presented below.

In one aspect, the invention provides a TGF-β MI mutant, characterized in that compared with wild-type TGF-β MI, the TGF-β MI mutant comprises mutation(s) at one or more amino acid residue positions selected from the group consisting of position 6, position 12, and position 20; wherein the numbering of the amino acid residues of the wild-type TGF-β RII refers to SEQ ID NO. 6.

Further, the TGF-β MI mutant according to the invention is characterized in that compared with the wild-type TGF-β RII, the mutant comprises one or more mutations selected from the group consisting of Q6N, D12T, and G20T.

Further, the TGF-β MI mutant according to the invention is characterized in that the mutant is capable of binding to TGF-β, and the TGF-β includes TGF-β1, TGF-β2 and TGF-β3.

Still further, the TGF-β MI mutant according to the invention is characterized in that compared with the wild-type TGF-β RII, the TGF-β MI mutant has less breakage and/or degradation when recombinantly expressed.

In a second aspect, the invention provides a fusion protein comprising two or more functional fragments, characterized in that at least one of the functional fragments has the amino acid sequence of the TGF-β RII mutant as described in the first aspect of the invention.

Further, the fusion protein according to the invention is characterized in that the two or more functional fragments function independently from each other.

Optionally, the functional fragments are linked to each other via a polypeptide linker (Linker).

Further, the fusion protein according to the invention is characterized in that the functional fragments further include an antibody or an antigen binding portion thereof, a receptor or a ligand binding portion thereof, a cytokine or a fragment thereof, a cytotoxin or a variant thereof, a label, or a tracer, or the like.

Still further, the fusion protein according to the invention is characterized in that the functional fragments specifically bind to a target selected from the group consisting of a target for tumor or cancer immunotherapy, a target for chronic infectious disease immunotherapy, and a target for autoimmune disease therapy.

Still further, the fusion protein according to the invention is characterized in that the target includes epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, STAT5, and the like.

In a third aspect, the invention provides a multifunctional active molecule having two or more functional activities, characterized in that at least one of the functional activities is a TGF-β binding activity which is conferred by a polypeptide fragment having the amino acid sequence of the TGF-β RII mutant as described in the first aspect of the invention.

Further, the multifunctional active molecule according to the invention is characterized in that the functional activities further include an antigen binding activity, a ligand binding activity, a cytokine activity, a cytotoxicity, or a labeling activity.

Further, the multifunctional active molecule according to the invention is characterized in that the functional activities further include binding activities to the following molecules: epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, STAT5, and the like.

In a fourth aspect, the invention provides an antibody-TGF-β RII conjugate molecule, characterized in that the antibody targets a target for tumor therapy, and the TGF-β RII has the amino acid sequence of the TGF-β RII mutant as described in the first aspect of the invention.

Further, the antibody-TGF-β RII conjugate molecule according to the invention is characterized in that the antibody specifically targets epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, or STAT5, preferably EGFR, VEGFR, PDGFR, FGFR, HER2, CTLA, CD20, CD133, PD-1, or PD-L1.

Further, the antibody-TGF-β RII conjugate molecule according to the invention is characterized in that the antibody is a murine antibody, a chimeric antibody, a humanized antibody, an Fab antibody, an Fab' antibody, an F(ab')2 antibody, an Fv antibody, a scFv antibody, or a nanobody. The antibody or fragment thereof provided by the invention is in any form, e.g., a monoclonal antibody, a single chain antibody, a single domain antibody, a bifunctional antibody, a nanobody, a fully or partially humanized antibody, or a chimeric antibody or the like. Alternatively, the antibody or fragment thereof may be a half-antibody or an antigen-binding fragment of the half-antibody, e.g., a scFv, a BsFv, a dsFv, a (dsFv)2, an Fab, an Fab', an F(ab')2, or a Fv. With respect to the fragment provided by the invention, preferably, the fragment may be any fragment of the antibody capable of binding to PD-L1. The antibody or antigen binding fragment thereof according to the invention may be a murine antibody, a chimeric antibody, a humanized antibody, an Fab, an Fab', an F(ab')2, an Fv, or a scFv.

Preferably, the antibody provided by the invention is IgA, IgD, IgE, IgG or IgM, more preferably IgG1. The fragment of the antibody is selected from the group consisting of a scFv, an Fab, an F(ab')2 and an Fv fragment of the antibody.

Preferably, the antibody or fragment thereof further comprises a human or murine constant region, preferably a human or murine light chain constant region (CL) and/or heavy chain constant region (CH). More preferably, the antibody or fragment thereof comprises a heavy chain constant region selected from the group consisting of IgG, IgA, IgM, IgD and IgE and/or a kappa or lambda type light chain constant region. According to particular embodiments of the invention, the antibody may be a monoclonal antibody, preferably a murine, chimeric, or humanized monoclonal antibody. More preferably, the heavy chain constant region of the monoclonal antibody is of an IgG1 or IgG4 subtype.

Further, the antibody-TGF-β RII conjugate molecule according to the invention is characterized in that the antibody is an anti-human PD-L1 antibody or antigen binding fragment thereof, wherein the anti-human PD-L1 antibody or antigen binding fragment thereof has CDR1 as shown in SEQ ID NO. 25, CDR2 as shown in SEQ ID NO. 26, and CDR3 as shown in SEQ ID NO. 27 in the heavy chain, and has CDR1 as shown in SEQ ID NO. 28, CDR2 as shown in SEQ ID NO. 29, and CDR3 as shown in SEQ ID NO. 30 in the light chain.

Furthermore, the antibody-TGF-β RII conjugate molecule according to the invention is characterized in that the antibody is an anti-human PD-L1 nanobody, wherein the amino acid sequence of the anti-human PD-L1 nanobody is as shown in SEQ ID NO. 20.

Further, the antibody-TGF-β RII conjugate molecule according to the invention is characterized in that the TGF-β RII is linked to the anti-human PD-L1 antibody via a linker peptide, wherein the linker peptide preferably comprises $(G_4S)n$, in which n is an integer from 1 to 4.

In a fifth aspect, the present invention provides a composition comprising the TGF-β RII mutant as described in the first aspect of the invention, the fusion protein as described in the second aspect of the invention, the multifunctional active molecule as described in the third aspect of the invention, or the conjugate molecule as described in the fourth aspect of the invention, and a pharmaceutically acceptable excipient.

In a sixth aspect, the invention provides a nucleic acid encoding the TGF-β RII mutant as described in the first aspect of the invention, the fusion protein as described in the second aspect of the invention, the multifunctional active molecule as described in the third aspect of the invention, or the conjugate molecule as described in the fourth aspect of the invention.

In a seventh aspect, the invention provides a recombinant vector comprising the nucleic acid as described in the sixth aspect of the invention.

In an eighth aspect, the invention provides a recombinant host cell comprising the nucleic acid as described in the sixth aspect of the invention, or the recombinant vector as described in the seventh aspect of the invention.

In a ninth aspect, the invention provides a method for producing a product, characterized in that the method includes producing a TGF-β RII mutant, a fusion protein thereof, a multifunctional active molecule thereof, or a conjugate molecule thereof using the nucleic acid as described in the sixth aspect, the recombinant vector as described in the seventh aspect, or the recombinant host cell as described in the eighth aspect of the invention.

In a tenth aspect, the invention provides a method for reducing or eliminating degradation or breakage of a recombinant protein comprising a TGF-β RII fragment, characterized in that the method comprises subjecting the coding region encoding the TGF-β RII fragment in the recombinant protein to mutagenesis, such that compared with wild-type TGF-β RII, the TGF-β RII encoded by the coding region comprises mutation(s) at one or more amino acid residue positions selected from the group consisting of position 6, position 12, and position 20; wherein the numbering of the amino acid residues of the wild-type TGF-β RII refers to SEQ ID NO. 6.

Further, the method for reducing or eliminating degradation or breakage of a recombinant protein according to the invention is characterized in that compared with the wild-type TGF-β RII, the TGF-β RII fragment comprises one or more mutations selected from the group consisting of Q6N, D12T, and G20T.

In an eleventh aspect, the invention provides a method for treating a disease, characterized in that the method comprises administering to a subject in need thereof an effective amount of a product selected from the group consisting of the TGF-β RII mutant as described in the first aspect, the fusion protein as described in the second aspect, the multifunctional active molecule as described in the third aspect, the conjugate molecule as described in the fourth aspect, the composition as described in the fifth aspect, the nucleic acid as described in the sixth aspect, the recombinant vector as described in the seventh aspect, or the recombinant cell as described in the eighth aspect of the invention.

Further, the method according to the invention is characterized in that the method is for preventing or treating a tumor or cancer, a chronic infectious disease, or an autoimmune disease.

Further, the method according to the invention is characterized in that the tumor or cancer is preferably selected from the group consisting of pharyngeal squamous carcinoma, non-small cell lung carcinoma, pancreatic cancer, liver cancer, urothelial cancer, colorectal cancer, and gastric cancer.

In a twelfth aspect, the invention provides use of a product in manufacturing a medicament, characterized in that the product comprises the TGF-β MI mutant as described in the first aspect, the fusion protein as described in the second aspect, the multifunctional active molecule as described in the third aspect, the conjugate molecule as described in the fourth aspect, the composition as described in the fifth aspect, the nucleic acid as described in the sixth aspect, the recombinant vector as described in the seventh aspect, or the recombinant cell as described in the eighth aspect of the invention.

Further, the use of a product in manufacturing a medicament according to the invention is characterized in that the medicament is for preventing or treating a tumor or cancer, a chronic infectious disease, or an autoimmune disease.

Further, the use of a product in manufacturing a medicament according to the invention is characterized in that the tumor or cancer is preferably selected from the group consisting of pharyngeal squamous carcinoma, non-small cell lung carcinoma, pancreatic cancer, liver cancer, urothelial cancer, colorectal cancer, and gastric cancer.

Definitions of certain terms are provided hereinafter to help the invention to be understood better. Other definitions are set forth throughout the DETAILED DESCRIPTION OF PREFERRED EMBODIMENTS part below.

Term "antibody" as used herein is intended to encompass a full-length antibody and any antigen-binding fragment (i.e., an antigen-binding portion) or single chain thereof. The full-length antibody refers to a glycoprotein comprising at least two heavy (H) chains and two light (L) chains, the heavy and light chains being linked by disulfide bonds. Each heavy chain is composed of a heavy chain variable region (abbreviated as VH) and a heavy chain constant region. The heavy chain constant region is composed of three domains, i.e., CH1, CH2, and CH3. Each light chain is composed of a light chain variable region (abbreviated as VL) and a light chain constant region. The light chain constant region is composed of one domain CL. The VH and VL regions can further be divided into hypervariable regions termed Complementarity Determining Regions (CDRs) and more conserved Framework Regions (FRs) which separate the CDRs. Each VH and VL is composed of three CDRs and four FRs, arranged in the order FR1, CDR1, FR2, CDR2, FR3, CDR3, FR4 from the amino terminus to the carboxyl terminus. The variable regions of the heavy and light chains comprise binding domains that interact with an antigen. The constant regions of an antibody can mediate the binding of the immunoglobulin to a tissue or factor in a host, including various immune system cells (e.g., effector cells) and the first component of the classical complement system (C1q).

Term "isolated antibody" as used herein refers to an antibody that is substantially free of other antibodies having specificities for different antigens.

Term "antigen-binding fragment" of an antibody (or abbreviated as portion of an antibody) as used herein refers to one or more fragments of an antibody that retain the ability to specifically bind antigen. It has been demonstrated that the antigen binding function of an antibody can be implemented by a fragment of the full-length antibody. Examples of a binding fragment encompassed within the "antigen binding portion" of an antibody include: (i) an Fab fragment, a monovalent fragment composed of VL, VH, CL and CH1; (ii) an F(ab')2 fragment, a bivalent fragment comprising two Fab fragments linked by a disulfide bridge at the hinge region; (iii) an Fd fragment composed of VH and CH1; (iv) an Fv fragment composed of the VL and VH of a single arm of an antibody; (v) a dAb fragment composed of VH (Ward et al, (1989) Nature 341: 544-546); (vi) an isolated Complementarity Determining Region (CDR); and (vii) a nanobody, a heavy chain variable region comprising a single variable domain and two constant domains. Furthermore, although the two domains VL and VH of an Fv fragment are encoded by different genes, they may be joined recombinantly via a synthetic linker to form a single protein chain, in which the VL and VH regions pair to form a monovalent molecule (referred to as a single chain Fc (scFv); see, e.g., Bird et al, (1988) Science 242: 423-426; and Huston et al., (1988) Proc. Natl. Acad. Sci. USA 85: 5879-5883). These single chain antibodies are also intended to be encompassed within the meaning of the term. These antibody fragments can be obtained using conventional techniques known to those skilled in the art, and can be functionally screened in the same manner as intact antibodies.

The antigen binding fragment of the invention includes those capable of specifically binding to an antigen. Examples of an antibody binding fragment include, for example, but are not limited to, an Fab, an Fab', an F(ab')2, an Fv fragment, a single chain Fv (scFv), and a single domain fragment.

An Fab fragment contains the constant domain of the light chain and the first constant domain (CH1) of the heavy chain. An Fab' fragments differs from an Fab fragment by the addition of a few residues at the carboxyl terminus of the heavy chain CH1 domain including one or more cysteines from the antibody hinge region. An F(ab') fragment is produced by cleavage of the disulfide bond at the hinge cysteines of an F(ab')2 pepsin digestion product. Additional chemical couplings of antibody fragments are known to those of ordinary skill in the art. Fab and F(ab')2 fragments lack the fragment crystallizable (Fc) region of an intact antibody, clear more rapidly from the circulation of animals, and may have less non-specific tissue binding than an intact antibody (see, e.g., Wahl et al, 1983, J. Nucl. Med. 24:316).

As is generally understood in the art, an "Fc" region is a fragment crystallizable constant region of an antibody that comprises no an antigen specific binding region. In IgG, IgA and IgD antibody isotypes, the Fc region consists of two identical protein fragments derived from the second and third constant domains of the two heavy chains of an antibody (CH2 and CH3 domains, respectively). The Fc regions of IgM and IgE contain three heavy chain constant domains (CH2, CH3, and CH4 domains) in each polypeptide chain.

An "Fv" fragment is the minimum fragment of an antibody that contains a complete target recognition and binding site. This region consists of a dimer of one heavy chain variable domain and one light chain variable domain in a tight, non-covalent association (VH-VL dimer). In this configuration, the three CDRs of each variable domain interact to define a target binding site on the surface of the VH-VL dimer. Generally the six CDRs confer target binding specificity to the antibody. However, in some instances even a single variable domain (or half of an Fv comprising only three CDRs specific for a target) can have the ability to recognize and bind a target, although at a lower affinity than the entire binding site.

A "single-chain Fv" or "scFv" antibody binding fragment comprises the VH and VL domains of an antibody, which are present in a single polypeptide chain. Generally, an Fv polypeptide further comprises a polypeptide linker between the VH and VL domains which enables the scFv to form a structure desired for target binding.

A "single domain fragment" is composed of a single VH or VL domain which exhibits sufficient affinity to an antigen. In a particular embodiment, the single domain fragment is camelized (see, e.g., Riechmann, 1999, Journal of Immunological Methods 231:25-38).

The antibody of the invention encompasses derivatized antibodies. For example, derivatized antibodies are typically modified by glycosylation, acetylation, pegylation, phosphorylation, amidation, derivatization by known protecting/ blocking groups, proteolytic cleavage, or attachment to cellular ligands or other proteins. Any of a number of chemical modifications can be made by known techniques including, but not limited to, specific chemical cleavage, acetylation, formylation, metabolic synthesis of tunicamycin, and the like. In addition, the derivatives may contain one or more unnatural amino acids, e.g., using the ambrx technique (see, e.g., Wolfson, 2006, Chem. Biol. 13 (10): 1011-2).

The polypeptide Linker, also called polypeptide linking arm and polypeptide Linker, is a polypeptide molecule used for linking two functional active molecules. Whether the two active components in a fusion protein can respectively form correct spacial structures and better exert biological functions is closely related to the linker sequence linking the two components in the fusion protein. Recombinantly produced fusion proteins require the Linker inserted into the fusion protein not to hinder the respective functions of the proteins of interest.

There have been many relevant studies on the design and selection of Linker sequences. Currently two types are majorly studied, i.e. (1) Linker in the form of a helix such as [A(EAAAK)nA]; and (2) Linker with low hydrophobicity and low charge effect, including peptide chains of different lengths which can form helices, flexible Linkers, staphylococcal protein A, and the like. The length of the Linker is another important factor, and a too long Linker may make the fusion protein sensitive to proteases, resulting in a reduced yield of active fusion protein during production; while a shorter Linker when used, may make the two molecules fused too close, affecting the function of the protein.

Compared with prior arts, the technical solutions of the invention have the following advantages.

First, the inventors identified the sites where antibody/TGF-β RII fusion protein molecules break and degrade, according to mass spectrometry analysis results of recombinant antibody/TGF-β RII fusion proteins in combination with bioinformatics analysis, and further verified the breaking and degrading sites through designing amino acid mutations. Accordingly, the technical problem that antibody/TGF-β RII fusion proteins are susceptible to degradation during recombinant expression is overcome.

Second, TGF-β RII was modified by the inventors through site-directed mutagenesis. Without changing the number of the amino acids of TGF-β RII and the length of TGF-β RII, the shielding or loss of function caused by too large difference in molecular weight when the TGF-β RII is fused/conjugated with a multi-subunit protein such as an antibody is avoided. Site-directed mutagenesis is performed on the amino acids at positions 6, 12, and 20 of TGF-β RII in the present disclosure, and when the TGF-β RII obtained is used as a component of a fusion protein, it not only maintains the specific binding activity to TGF-β, thereby capable of binding to TGF-β1, TGF-β2 and TGF-β3 effectively, but also retain the biological functions of TGF-β R, thereby capable of blocking the binding of TGF-β to TGF-β R in vivo, inhibiting the tumor-promoting activity of TGF-β, and having anti-tumor effects and functions.

Third, the antibody to be fused with TGF-β RII was engineered and screened also by the inventors. An nanobody with a relatively small molecular weight was adopted to fuse with TGF-β RII via a linker, so that both the difference in molecule size between the two components in the bifunctional fusion protein and the structure complexity of the recombinant bifunctional fusion protein are reduced, thereby providing an antibody/TGF-β MI bifunctional fusion protein which is more convenient for large-scale production with more stable quality and a preparation method thereof.

BRIEF DESCRIPTION OF THE DRAWINGS

Embodiments of the invention are described in detail below with reference to the attached figures, in which:

FIG. 2*a*: supernatants of fusion protein H182-MUT4-TGF-β RII and mutants thereof detected by reducing 12% polyacrylamide gel electrophoresis, in which:

- parent: the culture supernatant of cells expressing H182-MUT4-TGF-β RII;
- m1: the culture supernatant of cells expressing H182-MUT4-TGF-β RIIm1;
- m2: the culture supernatant of cells expressing H182-MUT4-TGF-β RIIm2;
- m3: the culture supernatant of cells expressing H182-MUT4-TGF-β RIIm3.

Figure 2A:
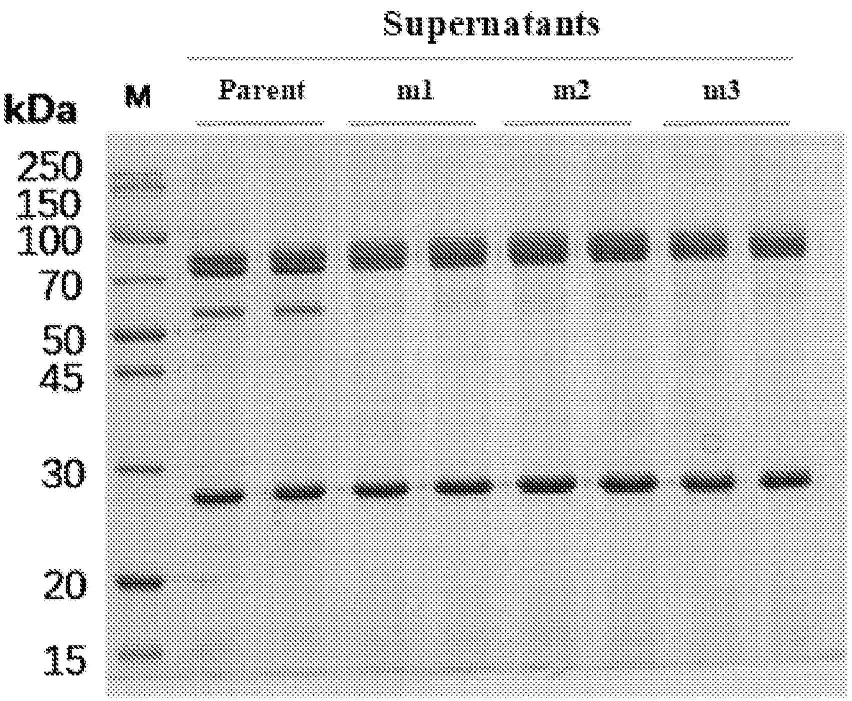

FIG. 2*b*: purified proteins of fusion protein H182-MUT4-TGF-β RII and mutants thereof detected by reducing 12% polyacrylamide gel electrophoresis, in which:

- original: the purified protein of H182-MUT4-TGF-β RII;
- m1: the purified protein of H182-MUT4-TGF-β RIIm1;
- m2: the purified protein of H182-MUT4-TGF-β RIIm2;
- m3: the purified protein of H182-MUT4-TGF-β RIIm3.

FIG. 3: a graph showing the results of recombinant protein H182-MUT4-TGF-β RII analyzed by SEC-HPLC.

Figure 4A:
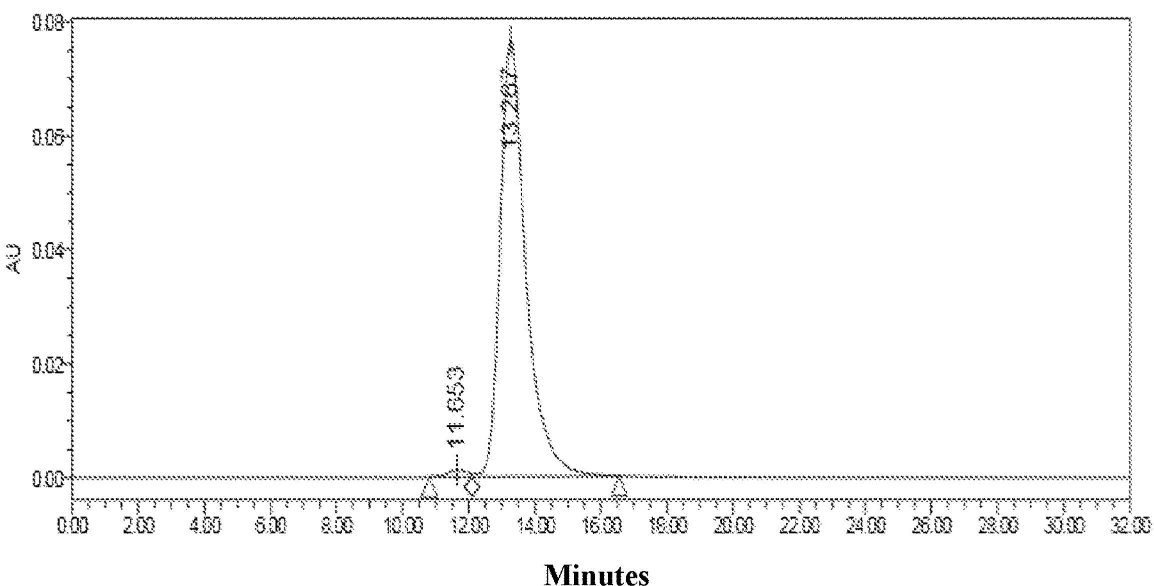

FIG. 4*a*: a graph showing the results of recombinant protein H182-MUT4-TGF-β RIIm1 analyzed by SEC-HPLC.

Figure 4B:
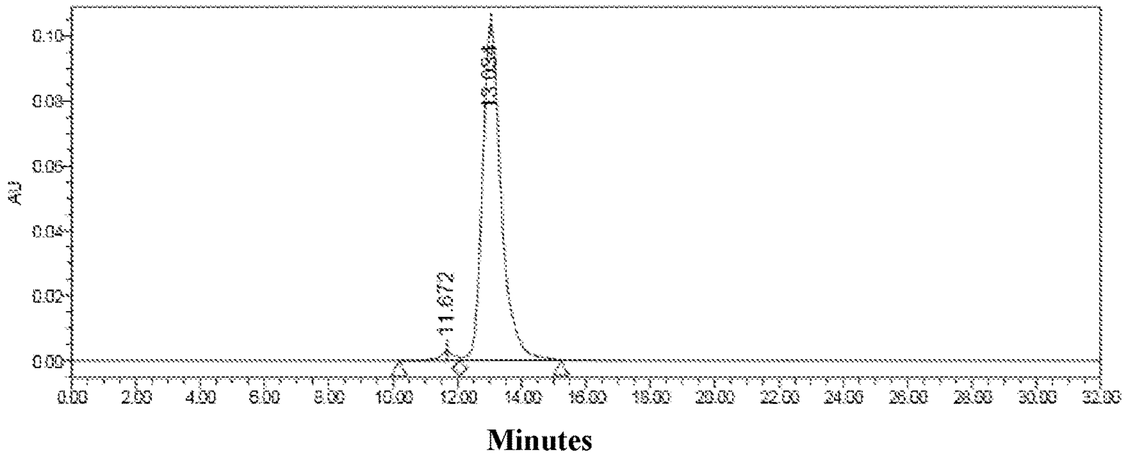

FIG. 4*b*: a graph showing the results of recombinant protein H182-MUT4-TGF-β RIIm2 analyzed by SEC-HPLC.

Figure 4C:
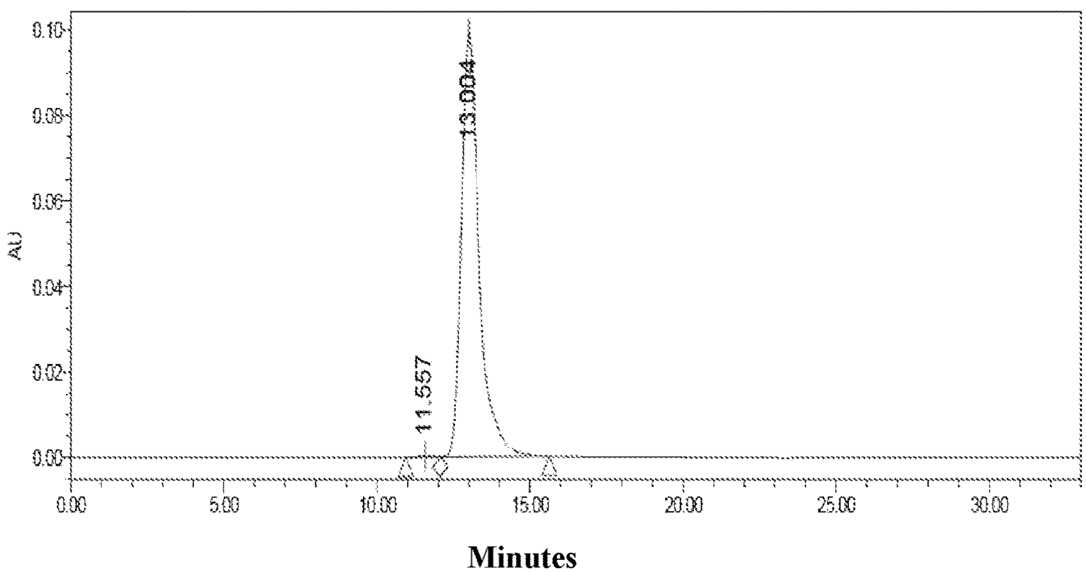

FIG. 4*c*: a graph showing the results of recombinant protein H182-MUT4-TGF-β RIIm3 analyzed by SEC-HPLC.

Figure 5:
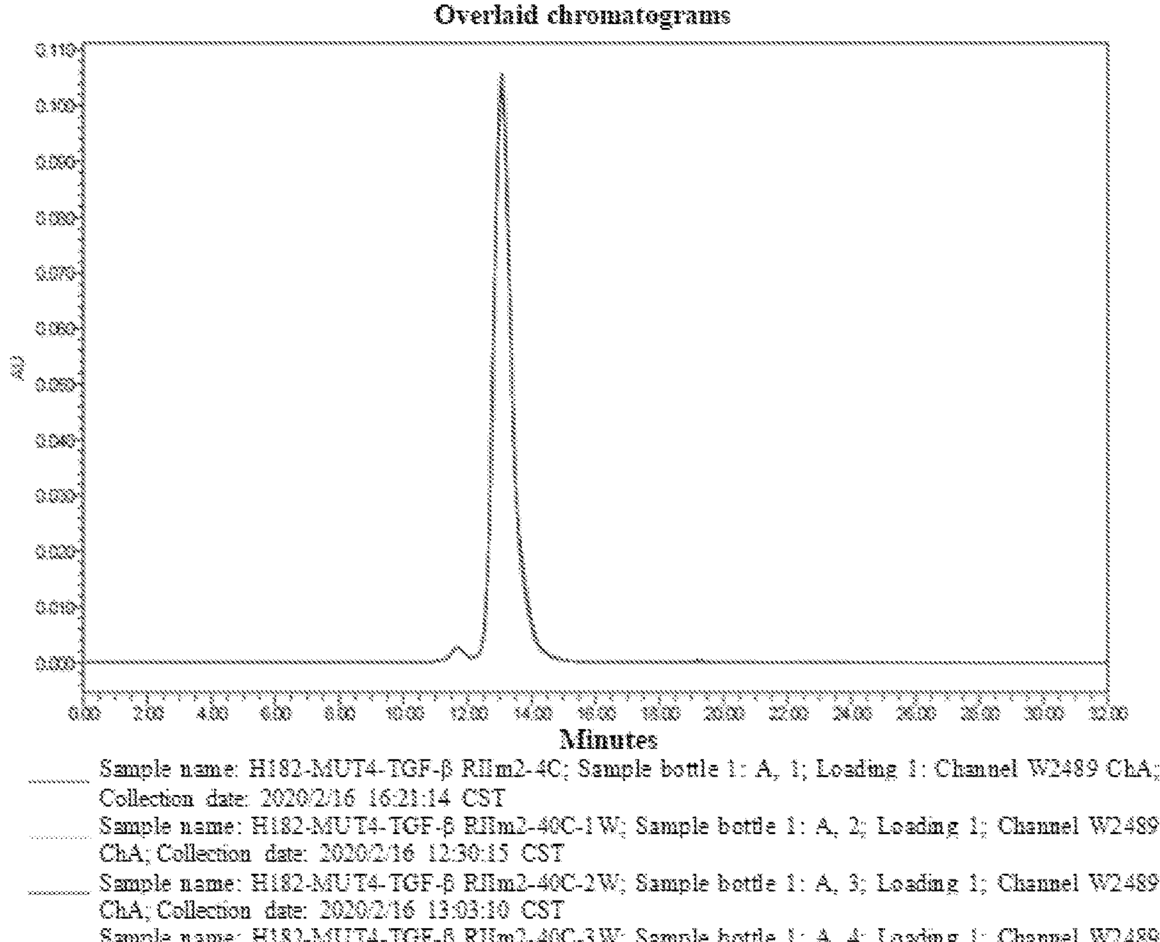

FIG. 5: a graph showing the results of samples of protein H182-MUT4-TGF-β RIIm2 placed at high temperature analyzed by SEC-HPLC, in which:

- red line: H182-MUT4-TGF-β RIIm2-40C, sample bottle 1: A, 1; loading 1: channel 2489 ChA; green line: H182-MUT4-TGF-β RIIm2-40C-1W, sample bottle 1: A, 2; loading 1: channel 2489 ChA;
- blue line: H182-MUT4-TGF-β RIIm2-40C-2W, sample bottle 1: A, 3; loading 1: channel 2489 ChA;
- gray lines: H182-MUT4-TGF-β RIIm2-40C-3W, sample bottle 1: A, 4; loading 1: channel 2489 ChA.

FIG. 6: a graph showing the results of samples of protein H182-MUT4-TGF-β RIIm2 repeatedly freezed and thawed analyzed by SEC-HPLC, in which:

- red line: H182-MUT4-TGF-β RIIm2-20C, sample bottle 1: A, 5; loading 1: channel 2489 ChA;
- green line: H182-MUT4-TGF-β RIIm2-20C-freezed and thawed once, sample bottle 1: A, 6; loading 1: channel 2489 ChA;
- blue line: H182-MUT4-TGF-β RIIm2-20C-freezed and thawed 2 times, sample bottle 1: A, 7; loading 1: channel 2489 ChA;
- gray lines: H182-MUT4-TGF-β RIIm2-20C-freezed and thawed 3 times, sample bottle 1: A, 8; loading 1: channel 2489 ChA.

Figure 7:
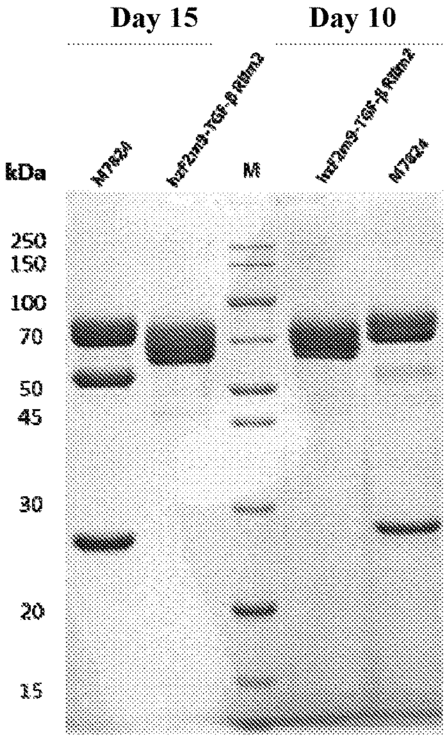

FIG. 7: culture supernatants of the anti-human PD-L1 antibody/TGF-β RII fusion protein for 10 and 15 days detected by reducing 12% polyacrylamide gel electrophoresis.

Figure 8:
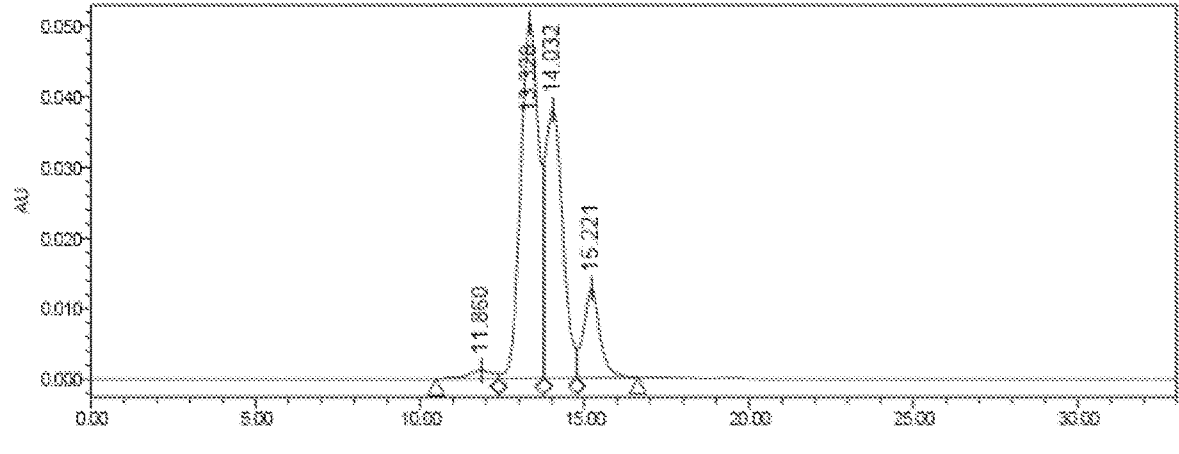

FIG. 8: a graph showing the results of purified protein from culture supernatant of M7824 for 15 days analyzed by SEC-HPLC.

Figure 9:
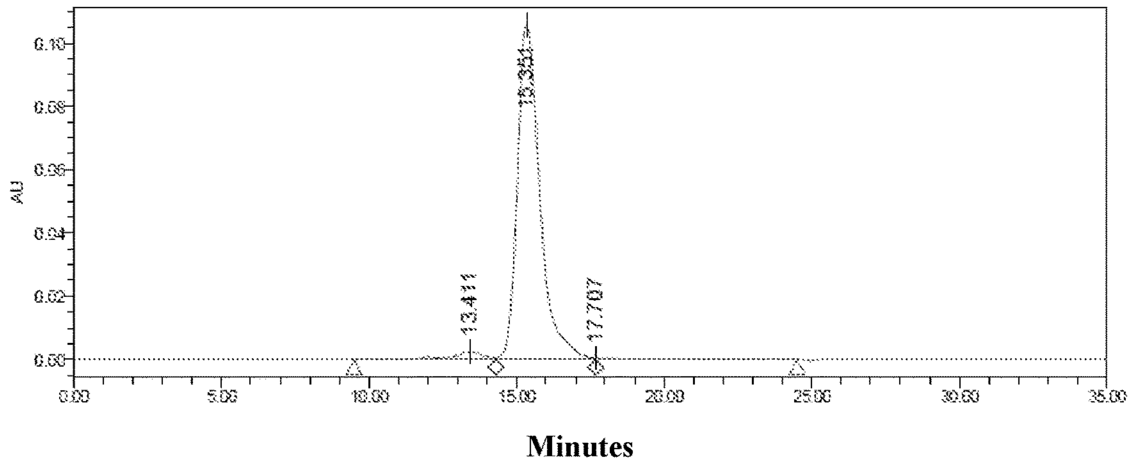

FIG. 9: a graph showing the results of purified protein from culture supernatant of hzF2-TGF-β RIIm2 for 15 days analyzed by SEC-HPLC.

Figure 10:
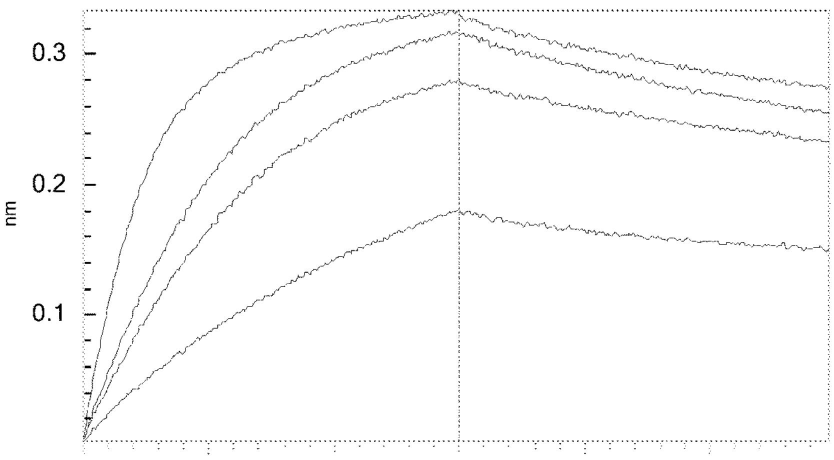

FIG. 10: a graph showing the results of affinity analysis of hzF2-TGF-β RIIm2 to recombinant human PD-L1 extracellular domain protein.

Figure 11:
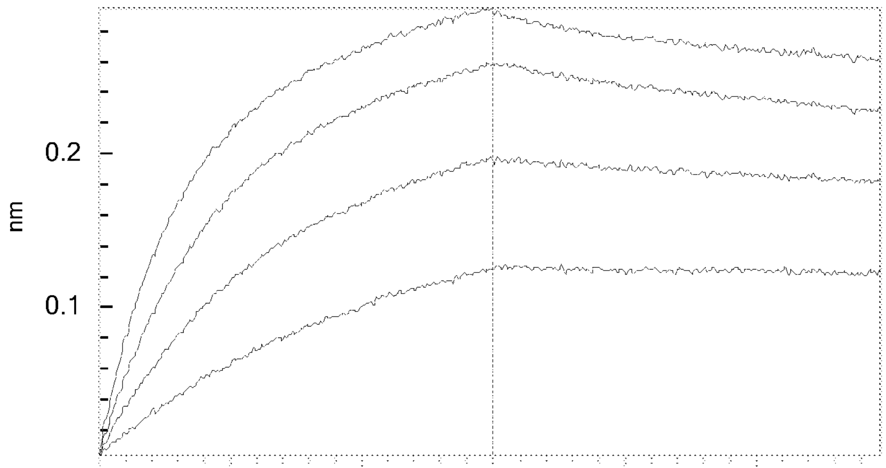

FIG. 11: a graph showing the results of affinity analysis of M7824 to recombinant human PD-L1 extracellular domain protein.

Figure 12:
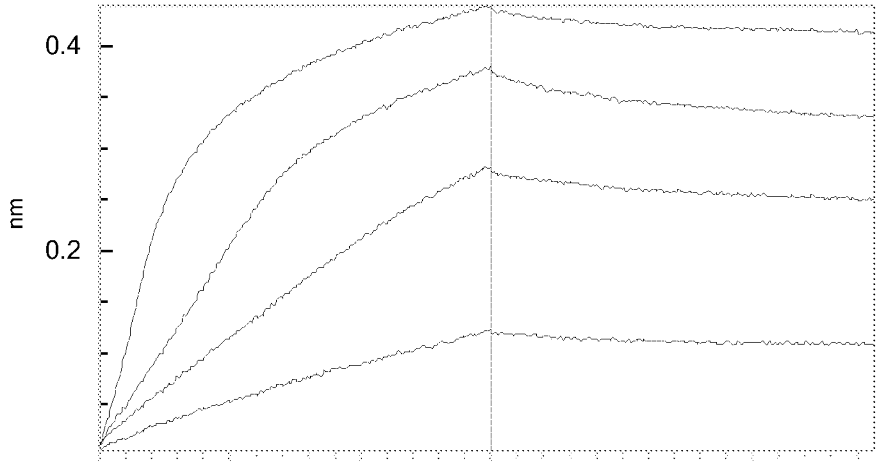

FIG. 12: a graph showing the results of affinity analysis of hzF2-TGF-β RIIm2 to recombinant human TGF-β 1 protein.

Figure 13:
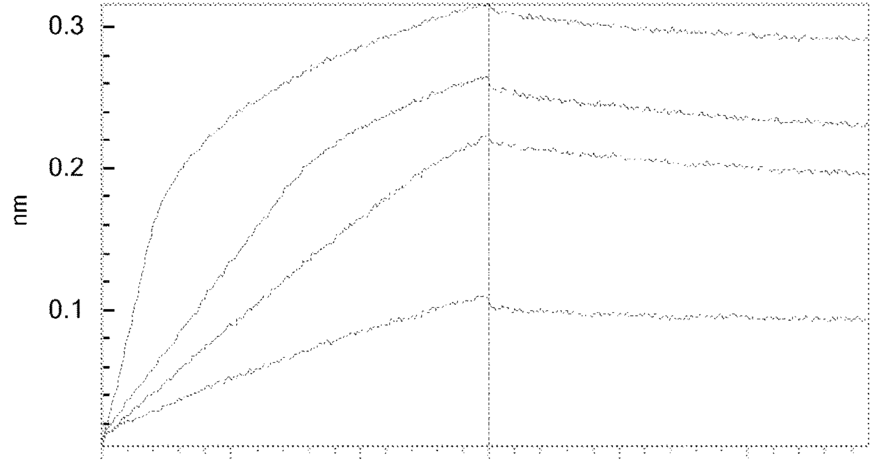

FIG. 13: a graph showing the results of affinity analysis of M7824 to recombinant human TGF-β 1 protein.

Figure 14:
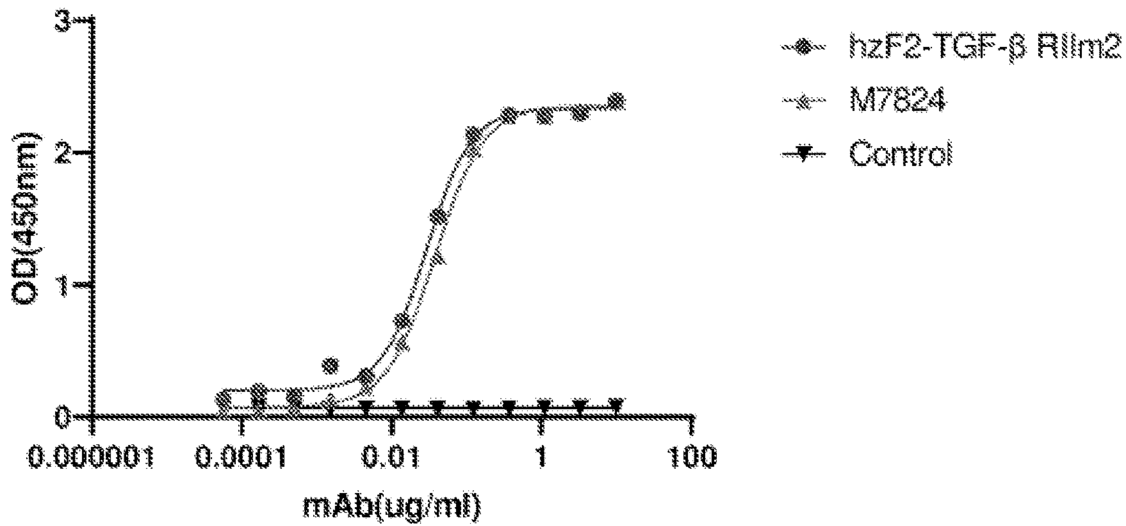

FIG. 14: a graph showing the results of binding activity of fusion protein hzF2-TGF-β RIIm2 to recombinant human PD-L1 extracellular domain protein detected by ELISA.

Figure 15:
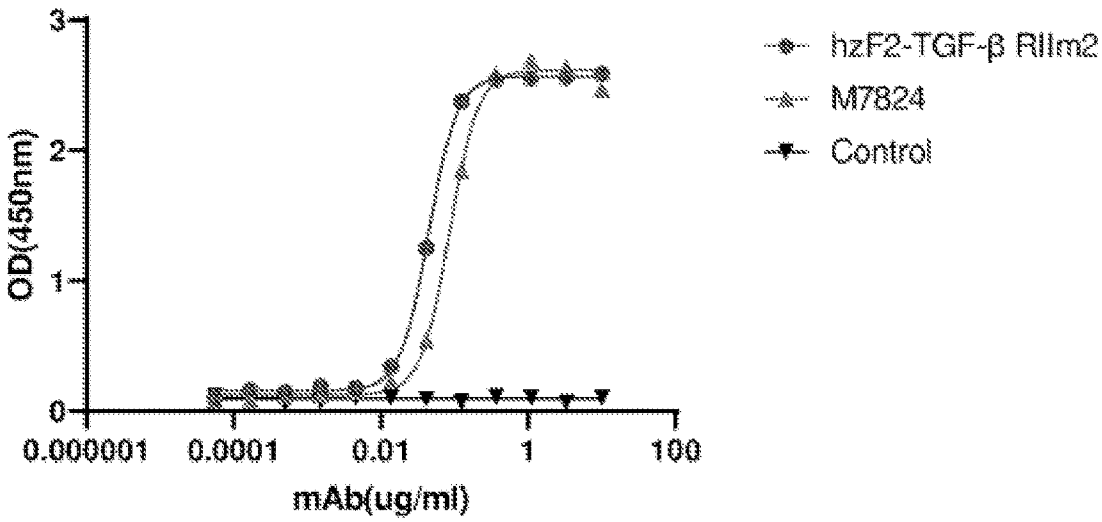

FIG. 15: a graph showing the results of binding activity of fusion protein hzF2-TGF-β RIIm2 to recombinant human TGF-β 1 protein detected by ELISA.

Figure 16:
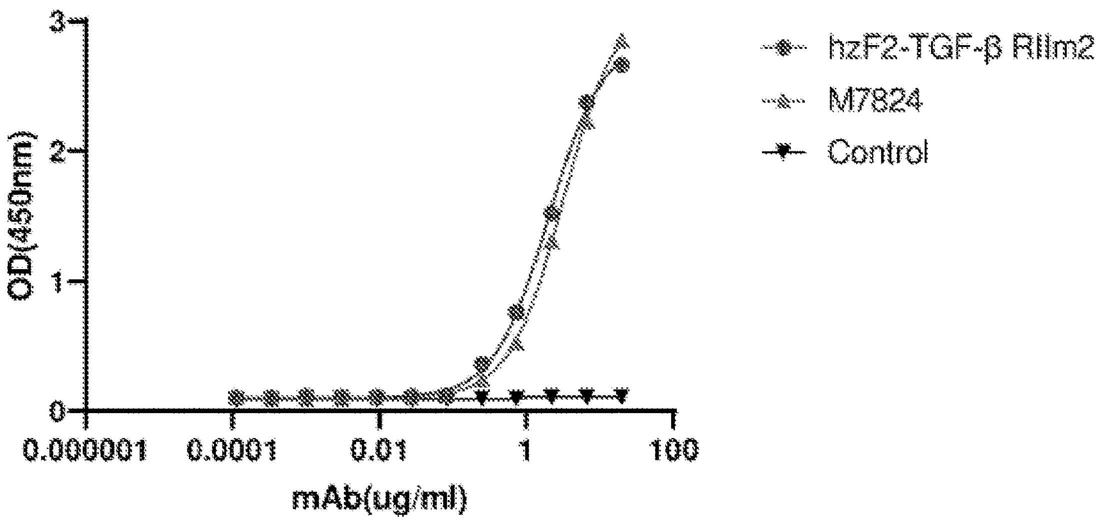

FIG. 16: a graph showing the results of binding activity of fusion protein hzF2-TGF-β RIIm2 to recombinant human TGF-β 2 protein detected by ELISA.

Figure 17:
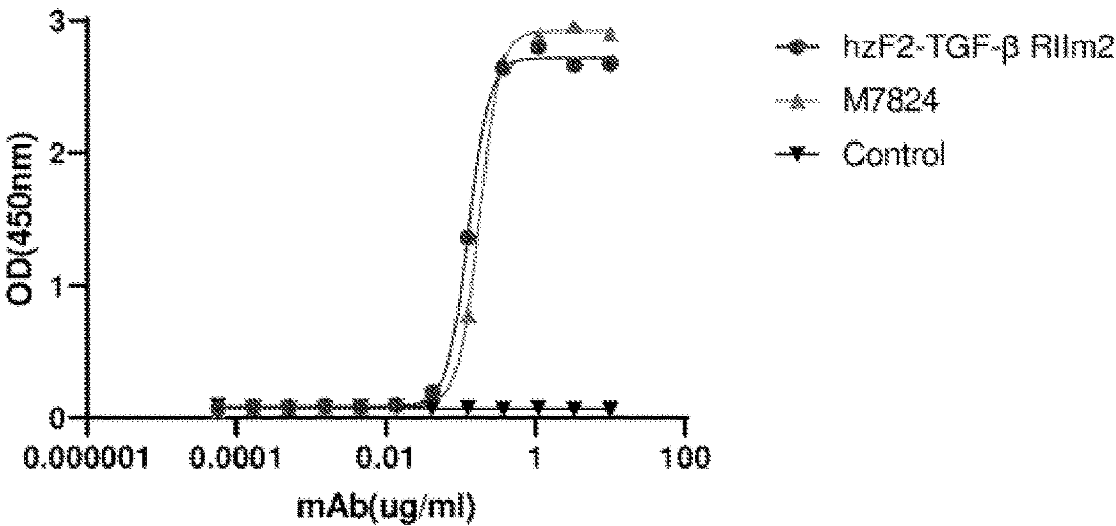

FIG. 17: a graph showing the results of binding activity of fusion protein hzF2-TGF-β RIIm2 to recombinant human TGF-β 3 protein detected by ELISA.

Figure 18:
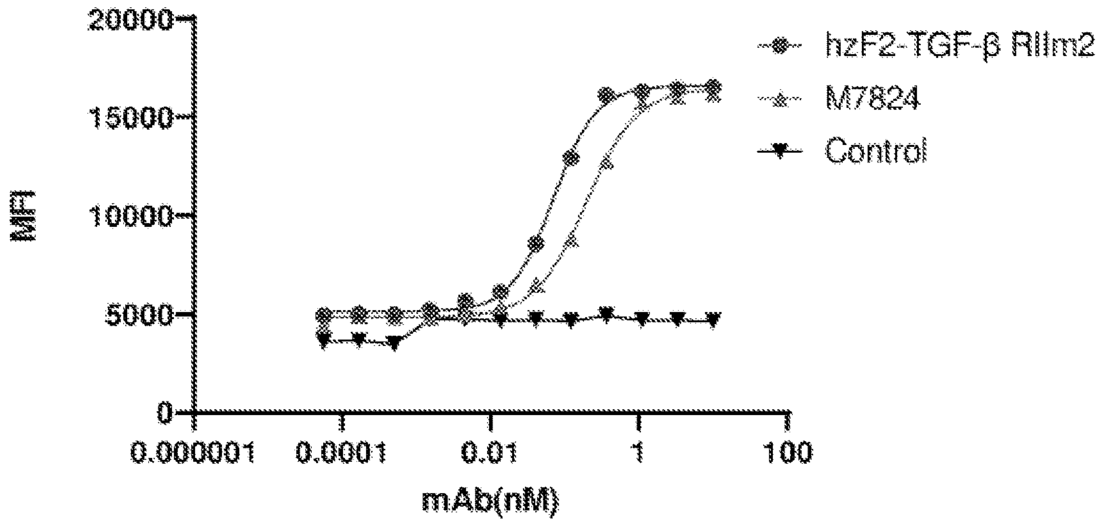

FIG. 18: a graph showing the results of binding activity of fusion protein hzF2-TGF-β RIIm2 to native PD-L1 protein on the cell surface detected by FASC.

Figure 19:
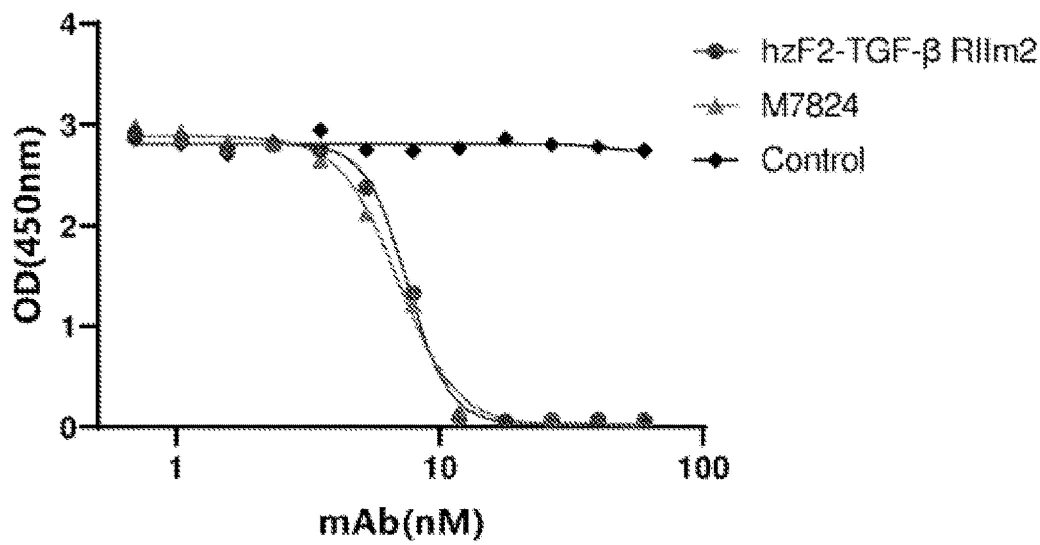

FIG. 19: inhibition effect of fusion protein hzF2-TGF-β RIIm2 on the binding of human PD-L1 to its receptor PD-1 detected by ELISA.

Figure 20:
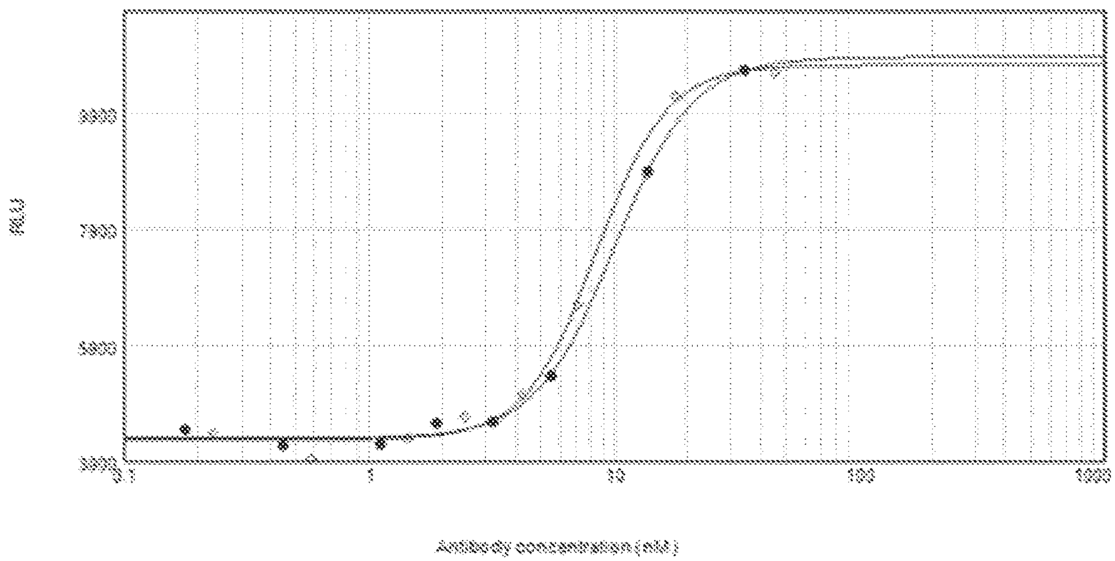

FIG. 20: detection of biological activity of fusion protein hzF2-TGF-β RIIm2.

Figure 21:
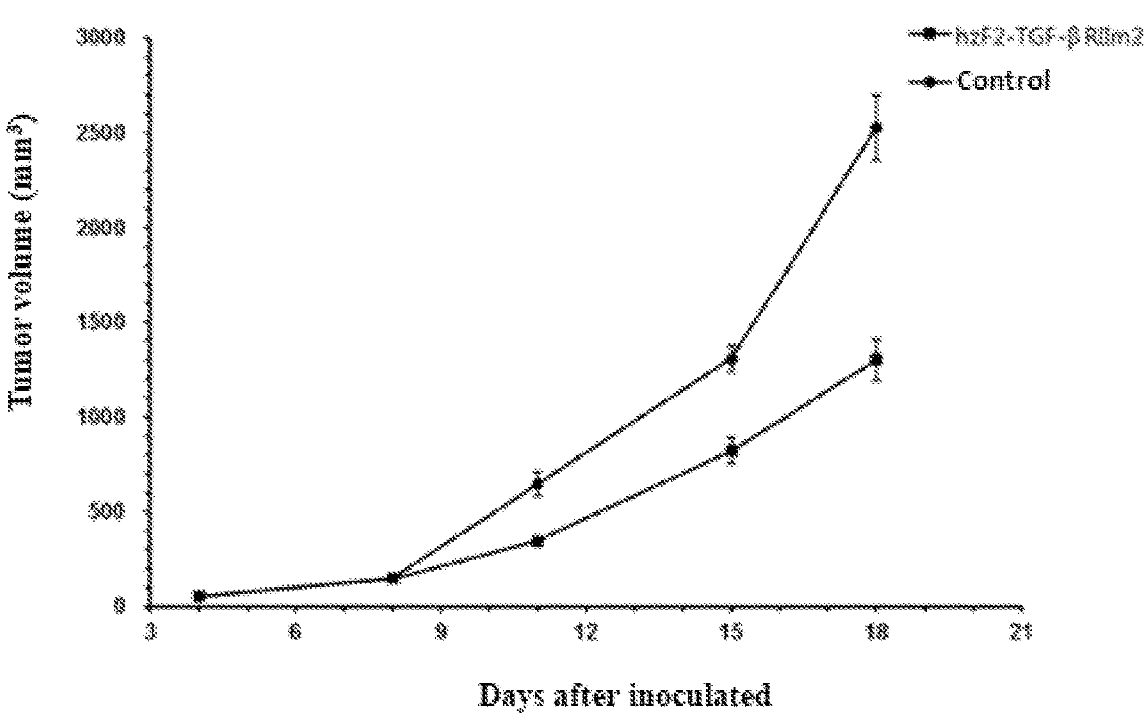

FIG. 21: statistics of tumor volume of subcutaneous transplantation tumors in PBMC immune reconstitution mice.

Figure 22:
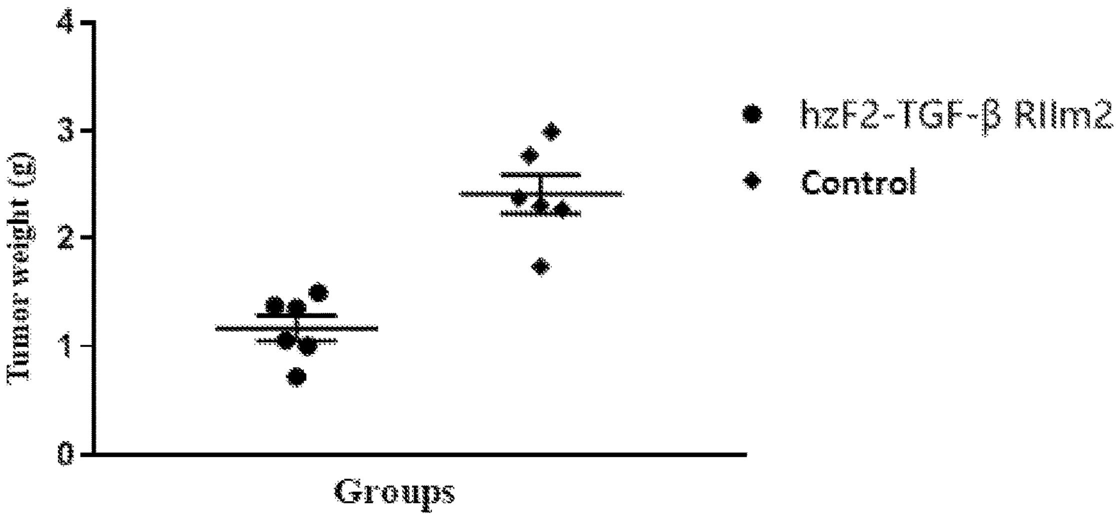

FIG. 22: statistics of tumor weight of subcutaneous transplantation tumors in PBMC immune reconstitution mice.

Figure 23:
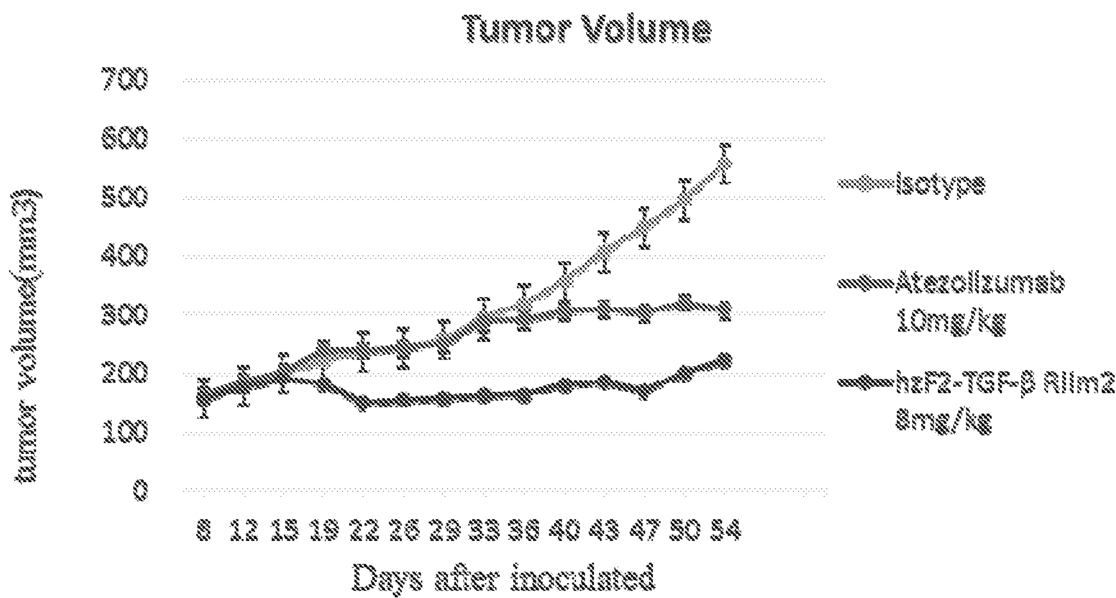

FIG. 23: a graph showing the results of evaluation of the antitumor activity of fusion protein hzF2-TGF-β RIIm2 in a tumor model of human CD34+ cord blood stem cell humanized mice subcutaneously inoculated with HCC827 cells.

DETAILED DESCRIPTION OF PREFERRED EMBODIMENTS

To solve the technical problem that TGF-β RII and fusion protein thereof are susceptible to degradation and breakage during recombinant expression, the invention provides a TGF-β RII mutant and a fusion protein thereof, wherein compared with the extracellular domain of the wild-type TGF-β RII as shown in SEQ ID NO. 6, the TGF-β RII mutant has mutation(s) at the position(s) selected from positions 6 (Gln), 12 (Asp) and 20 (Gly). The TGF-β RII mutant is capable of binding to TGF-β. The TGF-β MI mutant has less breakage and/or degradation when recombinantly expressed, compared with the wild-type TGF-β RII. An antibody/TGF-β MI bifunctional protein and a fusion protein thereof which are more convenient for large-scale production with more stable quality are provided.

The invention is illustrated below with reference to specific examples. It will be understood by those skilled in the art that these examples are merely illustrative of the present invention and do not limit the scope of the present invention in any way.

Experimental procedures in the following examples are all conventional ones, unless otherwise specified. Raw materials and reagents used in the following examples are all commercially available products, unless otherwise specified.

Example 1: Preparation of Samples of Anti-Human PD-L1 Antibody/TGF-β RII Fusion Protein and Control

1.1 Preparation of Anti-Human PD-L1 Antibody/TGF-β RII Fusion Protein

Using a PCR method, the nucleotide sequence (SEQ ID NO. 1) encoding the heavy chain of the PD-L1 antibody H182-MUT4 (MW22, from the patent application No. CN201911419802.5) was C-terminally linked to the nucleotide sequence (SEQ ID NO. 5) encoding the TGF-β RII extracellular domain via the nucleotide sequence (SEQ ID NO. 3) encoding a linker peptide, to obtain a sequence (SEQ ID NO. 9) encoding H182-MUT4-H-TGF-β RII comprising PD-L1 antibody heavy chain—TGF-β RII. The nucleotide sequence encoding H182-MUT4-H-TGF-β RII and the nucleotide sequence (SEQ ID NO. 7) encoding the light chain of the PD-L1 antibody (H182-MUT4-L) were ligated by enzymatic digestion and cloned into a stable expression vector containing a Glutamine Synthetase (GS) gene, to construct a eukaryotic expression vector of H182-MUT4-TGF-β RII for stable transfection. The vector was transferred into *Escherichia coli* cells for expansion, and a large amount of eukaryotic expression plasmids of H182-MUT4-TGF-β RII were isolated and obtained. The prepared eukaryotic expression plasmids of H182-MUT4-TGF-β RII were electrically transfected (Nucleofector IIb, Lonza) into CHO-K1 cells in suspension culture, and cells stably expressing fusion protein H182-MUT4-TGF-β RII were obtained through MSX pressure screening. The cells were cultured in fed-batch culture and observed for cell density and activity every day. Portions of culture supernatant of the cells were collected every day since day 9, and the supernatant was collected by high-speed centrifugation of all the cell culture broth when the cell activity was less than 20%. Part of the expression supernatant was purified using a Protein A affinity chromatography column and the anti-human PD-L1 antibody/TGF-β RII fusion protein H182-MUT4-TGF-β RII was obtained.

1.2 Preparation of Anti-Human PD-L1 Antibody/TGF-β RII Fusion Protein Control The genes of the light chain and the heavy chain—TGF-β RII of M7824 (see patent document WO2015/118175A2 for sequences) were totally synthesized artificially, ligated by enzymatic digestion and cloned into a stable expression vector containing a Glutamine Synthetase (GS) gene, to construct a eukaryotic expression vector for stable transfection. The vector was electrically transfected (Nucleofector IIb, Lonza) into CHO-K1 cells in suspension culture, and cells stably expressing the recombinant protein M7824 were obtained through MSX pressure screening. The cells were cultured for expressing the protein, and the recombinant protein M7824 was obtained and used as a control.

Figure 1:
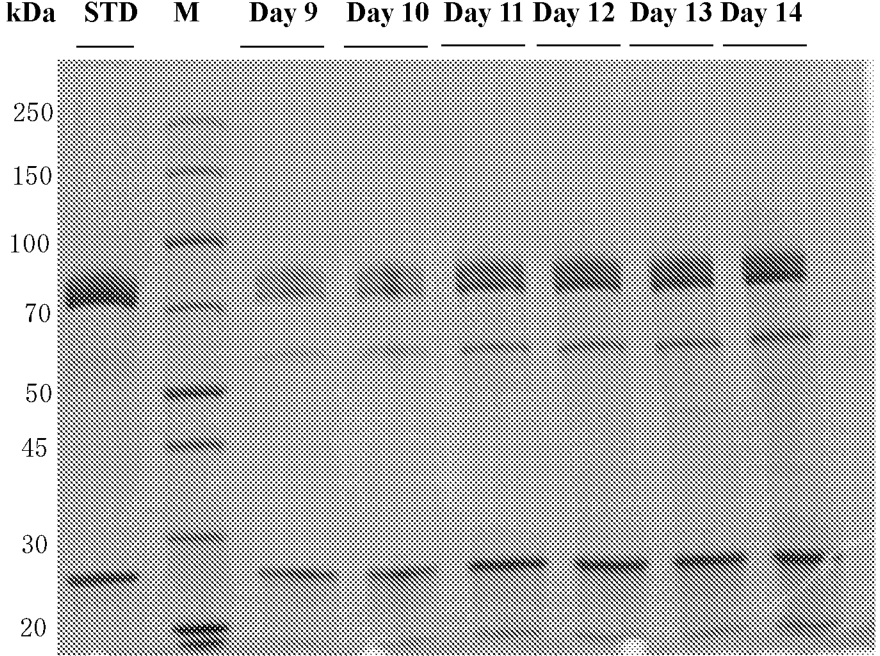
FIG. 1: a graph showing the results of culture supernatant of cells expressing fusion protein H182-MUT4-TGF-β RII for 9-14 days detected by reducing 12% polyacrylamide gel electrophoresis (SDS-PAGE).

Example 2: Analysis of Breakage Sites in H182-MUT4-TGF-β RII 2.1 Analysis of H182-MUT4-TGF-β RII by SDS-PAGE Electrophoresis The expression supernatant of H182-MUT4-TGF-β RII was subjected to electrophoretic analysis by reducing SDS-PAGE. The results showed (FIG. 1) there were three distinct bands in electrophoresis gel, of which the band having a molecular weight greater than 70 kDa was the protein chain with heavy chain fused of H182-MUT4-TGF-β RII, the band having a molecular weight between 20 and 30 kDa was the light chain of the anti-PD-L1 antibody H182-MUT4, while the distinct protein band between 50-70 kDa of the protein marker was presumably the heavy chain of H182-MUT4 off which TGF-β RII had shed. The proportion of the band of the broken protein increased with the culture time prolonging. The analysis results of M7824 were similar to those of H182-MUT4-TGF-β RII and had the problem of band due to breakage also.

2.2 Analysis of Breakage Sites in H182-MUT4-TGF-β RII by Mass Spectrometry

The bands having a molecular weight of 50-70 KDa in SDS-PAGE electrophoresis gel were recovered. Decolorizing buffer was added into the sample for an adequate decoloration, and reducing buffer was added to perform reducing treatment. Afterwards, tyrisin was added and enzymatic digestion was performed at 37° C. overnight. Then the enzymatic digestion products were extracted and desalted; and finally the peptide fragments were re-dissolved in 0.1% formic acid aqueous solution for subsequent mass spectrometry. For the mass spectrometry, an appropriate amount of the sample of peptide fragments was subjected to chromatographic resolution using an Easy nLC 1200 system (Thermo Scientific) at nanoliter flow rate. The peptide fragments were resolved and then analyzed by DDA (data dependent acquisition) mass spectrometry using a Q-exactive Plus mass spectrometer (Thermo Scientific). Finally, MaxQuant 1.6.1.0 software for mass spectral database retrieval was used for alignment analysis. The analysis results by mass spectrometry are provided in Table 1 below, and showed that the sample lacked the amino acids at the position 478 and later. In combination with the speculation that the sites digested by tyrisin possibly locate after the amino acids Lys and Arg, it was thought after comprehensive analysis that the heavy chain of H182-MUT4-TGF-β RII may break at amino acid position 477/478.

TABLE 1

Analysis results of H182-MUT4-TGF-B RII by Mass Spectrometry

| Sequence | Length | Proteins | Start position | End position |
|---|---|---|---|---|
| VVSVLTVLHQDWLNGK (SEQ ID NO. 50) | 16 | H182-MUT4-H-TGF-β RII | 304 | 319 |
| WQQGNVFSCSVMHEALHNHYTQK (SEQ ID NO. 51) | 23 | H182-MUT4-H-TGF-β RII | 419 | 441 |
| NQVSLTCLVK (SEQ ID NO. 52) | 10 | H182-MUT4-H-TGF-β RII | 363 | 372 |
| FNWYVDGVEVHNAK (SEQ ID NO. 53) | 14 | H182-MUT4-H-TGF-β RII | 277 | 290 |
| DTLMISR (SEQ ID NO. 54) | 7 | H182-MUT4-H-TGF-β RII | 251 | 257 |
| GPSVFPLAPSSK (SEQ ID NO. 55) | 12 | H182-MUT4-H-TGF-β RII | 124 | 135 |
| EVQLVQSGAEVK (SEQ ID NO. 56) | 12 | H182-MUT4-H-TGF-β RII | 1 | 12 |
| VTITADTSTNTAYMELSSLR (SEQ ID NO. 57) | 20 | H182-MUT4-H-TGF-β RII | 68 | 87 |
| DIYMHWVQQAPGK (SEQ ID NO. 58) | 13 | H182-MUT4-H-TGF-β RII | 31 | 43 |
| EPQVYTLPPSR (SEQ ID NO. 59) | 11 | H182-MUT4-H-TGF-β RII | 347 | 357 |
| GLEWMGR (SEQ ID NO. 60) | 7 | H182-MUT4-H-TGF-β RII | 44 | 50 |
| ALPAPIEK (SEQ ID NO. 61) | 8 | H182-MUT4-H-TGF-β RII | 329 | 336 |
| THTCPPCPAPELLGGPSVFLFPPKPK (SEQ ID NO. 62) | 26 | H182-MUT4-H-TGF-β RII | 225 | 250 |
| GFYPSDIAVEWESNGQPENNYK (SEQ ID NO. 63) | 22 | H182-MUT4-H-TGF-β RII | 373 | 394 |
| EPQVYTLPPSRDELTK (SEQ ID NO. 64) | 16 | H182-MUT4-H-TGF-β RII | 347 | 362 |

TABLE 1-continued

| Analysis results of H182-MUT4-TGF-B RII by Mass Spectrometry | | | | |
|---|---|---|---|---|
| Sequence | Length | Proteins | Start position | End position |
| TTPPVLDSDGSFFLYSK (SEQ ID NO. 65) | 17 | H182-MUT4-H-TGF-β RII | 395 | 411 |
| IDPANANTK (SEQ ID NO. 66) | 9 | H182-MUT4-H-TGF-β RII | 51 | 59 |
| SLSLSPGAGGGGSGGGGSGGGGS GGGGSGIPPHVQK (SEQ ID NO. 67) | 36 | H182-MUT4-H-TGF-β RII | 442 | 477 |
| SCDKTHTCPPCPAPELLGGPSVFLF PPKPK (SEQ ID NO. 68) | 30 | H182-MUT4-H-TGF-β RII | 221 | 250 |

Example 3: Design, Expression and Analysis of Anti-Human PD-L1 Antibody/TGF-β RII Fusion Protein Mutants 3.1 Design and Expression of Anti-Human PD-L1 Antibody/TGF-β RII Fusion Protein Mutants According to the speculation about the sites where breakage occurred, glycosylation sites before and after the N-terminal enzyme cleavage sites of TGF-β RII were designed to realize the protection of the cleavage sites and prevent the occurrence of cleavage. The design of mutants is provided in Table 2. The nucleotide sequence encoding the TGF-β RII extracellular domain in the expression vector of anti-human PD-L1 antibody/TGF-β RII fusion protein H182-MUT4-TGF-β RII was subjected to site-directed mutagenesis using StarMut gene site-directed mutagenesis kit (Cat: T111-01, GenStar), to obtain expression plasmids of the mutants. The plasmids were then transferred into *Escherichia coli* cells for expansion, and plasmids of anti-human PD-L1 antibody/TGF-β RII fusion protein mutants, i.e., H182-MUT4-TGF-β RIIm1, H182-MUT4-TGF-β RIIm2, and H182-MUT4-TGF-β RIIm3, were obtained. The prepared plasmids of H182-MUT4-TGF-β RIIm1, H182-MUT4-TGF-β RIIm2 and H182-MUT4-TGF-β RIIm3 were electrically transfected (Nucleofector IIb, Lonza) into CHO-K1 cells in suspension culture, and cells stably expressing PD-L1 antibody/TGF-β MI fusion protein mutants were obtained through MSX pressure screening. The cells expressing H182-MUT4-TGF-β MI and its mutants H182-MUT4-TGF-β RIIm1, H182-MUT4-TGF-β RIIm2 and H182-MUT4-TGF-β RIIm3 were cultured in fed-batch culture and observed for cell density and activity every day. The supernatants were collected by high-speed centrifugation of all the cell culture broths when the cell activity was less than 20%. Parts of the supernatants were purified using a Protein A affinity chromatography column and the fusion protein H182-MUT4-TGF-β RII and its mutants were obtained.

TABLE 2

| Design of mutations in the sequence of TGF-β RII extracellular domain | |
|---|---|
| H182-MUT4-H-TGF-β RII | Mutation Site |
| H182-MUT4-H-TGF-β RII m1 | G490T |
| H182-MUT4-H-TGF-β RII m2 | Q476N |
| H182-MUT4-H-TGF-β RII m3 | D482T |

3.2 Detection of H182-MUT4-TGF-β RII and Mutants Thereof by SDS-PAGE Electrophoresis Samples of the expression supernatants and purified proteins of the fusion protein H182-MUT4-TGF-β RII and mutants thereof were subjected to reducing SDS-PAGE electrophoresis. The results showed (FIG. 2*a* and FIG. 2*b*) there were two distinct bands in electrophoresis gel of the protein mutants of H182-MUT4-TGF-β RII, in which the band having a molecular weight greater than 70 kDa was the protein chain with heavy chain fused of the respective H182-MUT4-TGF-β RII mutant, and the band having a molecular weight between 20 and 30 kDa was the light chain of the anti-PD-L1 antibody H182-MUT4, while the band between 50-70 kDa of the protein marker which was the heavy chain of H182-MUT4 off which TGF-β RII had shed disappeared.

3.3 Detection of H182-MUT4-TGF-β RII and Mutants Thereof by SEC-HPLC

Samples of the proteins H182-MUT4-TGF-β RII and its mutants H182-MUT4-TGF-β RIIm1, H182-MUT4-TGF-β RIIm2 and H182-MUT4-TGF-β RIIm3 were subjected to SEC-HPLC analysis. The results showed that H182-MUT4-TGF-β RII had obvious characteristic peaks of degradation fragments (FIG. 3, and Table 3), and upon mutation modification, the degradation problem was solved: the characteristic peaks of degradation fragments disappeared, and the purity of main HPLC peaks obviously increased (FIG. 4*a*, FIG. 4*b*, and FIG. 4*c*, and Table 3).

TABLE 3

Purity of the bifunctional proteins anti-human PD-L1 antibody/TGF-β RII fusion proteins detected by SEC-HPLC

| | SEC-HPLC (%) | | | |
|---|---|---|---|---|
| | Peak 1 | Peak 2 (main peak) | Peak 3 | Peak 4 |
| H182-MUT4-TGF-β RII | 2.9 | 59.57 | 30.76 | 6.77 |
| H182-MUT4-TGF-β RIIm1 | 1.13 | 98.87 | / | / |
| H182-MUT4-TGF-β RIIm2 | 1.99 | 98.01 | / | / |
| H182-MUT4-TGF-β RIIm3 | 0.31 | 99.69 | / | / |

Example 4: Stability Detection of Anti-Human PD-L1 Antibody/TGF-β RII Fusion Protein Mutant Samples of the bifunctional protein H182-MUT4-TGF-β RIIm2 were placed at 40° C. for three weeks, and one tube of the samples was taken and detected for stability each week. In addition, samples of the protein were repeatedly freezed and thawed at −20° C. for 3 times, and one of the samples was detected for freeze-thaw stability each time. The samples treated and a control sample always placed at 4° C. were detected for purity by SEC-HPLC, to verify their stability. The results are shown in FIG. 5 and FIG. 6. As shown, the purity of the samples placed at the high temperature and subjected to repeatedly freezing-thawing was basically consistent with that of the control sample, indicating the product was stable and no breakage occurred.

Example 5: Affinity Detection of the Anti-Human PD-L1 Antibody/TGF-β RII Fusion Proteins Antibody affinity was detected by an assay including capturing antibody Fc fragment with anti-human IgG Fc capture (AHC) biosensors on Octet QKe system instrument from Fortebio. For the assay, each of the bifunctional proteins H182-MUT4-TGF-β RII, H182-MUT4-TGF-β H182-MUT4-TGF-β RIIm2, and H182-MUT4-TGF-β RIIm3, as well as H182-MUT4 and TGF-β RII-hFc (Cat: CC10, Novoprotein Scientific Inc.) was diluted to 5 μg/ml in PBS, and was allowed to flow through the surface of an AHC biosensor (Cat.: 18-0015, PALL) for 120 s. Recombinant human PD-L1-his protein and recombinant human TGF-β 1 protein (Cat: CA59, Novoprotein Scientific Inc.) were used as the mobile phase in a concentration of 60 nM. The binding time was 300 s and the dissociation time was 300 s. When the assay was finished, data from which the response values of blank control had been deducted were fitted to a 1:1 Langmuir binding model using software, and then kinetic parameters for antigen-antibody binding were calculated. The results are provided in Table 4. As shown, the affinities of the bifunctional proteins H182-MUT4-TGF-β RII, H182-MUT4-TGF-β RIIm1, H182-MUT4-TGF-β RIIm2, and H182-MUT4-TGF-β RIIm3 to PD-L1 and TGF-β 1 were not obviously different from the affinities of H182-MUT4 and TGF-β RII-hFc to PD-L1 and TGF-β 1.

TABLE 4

Detection results of affinity of the bifunctional proteins anti-human PD-L1 antibody/TGF-β RII fusion proteins

| | KD value (M) | |
|---|---|---|
| | PD-L1 | TGFβ1 |
| H182-MUT4-TGF-β RII | 3.81E−10 | 1.45E−09 |
| H182-MUT4-TGF-β RIIm1 | 2.97E−10 | 1.14E−09 |
| H182-MUT4-TGF-β RIIm2 | 3.05E−10 | 1.34E−09 |
| H182-MUT4-TGF-β RIIm3 | 3.11E−10 | 1.22E−09 |
| H182-MUT4 | 4.33E−10 | / |
| TGF-β RII-hFc | / | 1.24E−09 |

Example 6: Design and Expression of Anti-Human PD-L1 Nanobody/TGF-β RII Fusion Protein Mutant Using a PCR method, the nucleotide sequence (SEQ ID NO. 19) encoding the humanized anti-human PD-L1 nanobody hzF2 (from patent application No.: CN202010324761.8) was C-terminally linked to the nucleotide sequence (SEQ ID NO. 13) encoding TGF-β RIIm2 via the nucleotide sequence encoding a linker peptide (SEQ ID NO. 21), to obtain a sequence (SEQ ID NO. 23) encoding hzF2-TGF-β RIIm2 comprising PD-L1 nanobody—TGF-β RIIm2. The nucleotide sequence was cloned into a stable expression vector containing a Glutamine Synthetase (GS) gene through enzyme digestion sites, to construct a eukaryotic expression vector of hzF2-TGF-β RIIm2 for stable transfection. The vector was transferred into *Escherichia coli* cells for expansion, and a large amount of eukaryotic expression plasmids of fusion protein hzF2-TGF-β RIIm2 were isolated and obtained. The prepared eukaryotic expression plasmids were electrically transfected (Nucleofector IIb, Lonza) into CHO-K1 cells in suspension culture, and cells stably expressing the fusion protein hzF2-TGF-β RIIm2 were obtained through MSX pressure screening. The cells were cultured for expression and purification, and the fusion protein mutant hzF2-TGF-β RIIm2 was obtained.

Example 7: Purity Detection of the Fusion Protein hzF2 TGF-β RIIm2

Cells expressing M7824 and hzF2-TGF-β RIIm2 were cultured in fed-batch culture and observed for cell density and activity every day. Portions of cell culture broths were collected in the mid-term of culture (day 10), and the remaining cell culture broths were collected in the late-term of culture when the cell activity was less than 20% (day 15). Supernatants were collected by high-speed centrifugation of the culture broths, and then purified using a Protein A affinity chromatography column. The purified expression supernatants were then subjected to protein quantification, and subpackaged for use. The expression supernatants were detected by reducing SDS-PAGE electrophoresis and SEC-HPLC. The SDS-PAGE results (FIG. 7) showed there were three distinct bands in electrophoresis gel of M7824, in which the band having a molecular weight greater than 70 kDa was the protein chain with fused heavy chain of M7824, the band having a molecular weight between 20 and 30 kDa was the light chain of M7824, while the distinct protein band between 50-70 kDa of the protein marker was presumably the heavy chain of M7824 off which TGF-β RII had shed. The proportion of the band of the broken protein increased with the extension of culture time. In contrast, in the electrophoresis gel of hzF2-TGF-β RIIm2, there was one distinct main band between 50 and 70 kDa, without any other obvious protein bands. The identification results by SEC-HPLC are shown in FIG. 8 and FIG. 9, and Table 5. As shown, M7824 had distinct peaks of fragments having low molecular weight, while hzF2-TGF-β RIIm2 had obviously reduced degradation.

TABLE 5

Purity of the anti-human PD-L1 antibody/TGF-β RII fusion protein detected by SEC-HPLC

| | SEC-HPLC (%) | | | |
|---|---|---|---|---|
| | Peak 1 | Peak 2 | Peak 3 | Peak 4 |
| M7824 | 1.65 | 50.47 | 36.57 | 11.31 |
| hzF2-TGF-β RIIm2 | 3.23 | 96.08 | 0.69 | |

Example 8: Affinity Analysis of the Fusion Protein hzF2-TGF-β RIIm2

Antibody affinity was detected by an assay including capturing antibody Fc fragment with anti-human IgG Fc capture (AHC) biosensors on Octet QKe system instrument from Fortebio. For the assay, each of the proteins (hzF2-TGF-β RIIm2 and M7824) was diluted to 4 μg/ml in PBS, and was allowed to flow through the surface of an AHC biosensor (Cat.: 18-0015, PALL) for 120 s. Recombinant human PD-L1-his protein (Accession No.: NP_054862.1, 19 aa-238 aa) and human TGF-β 1 (Cat: CA59, Novoprotein Scientific Inc.) were used as the mobile phase. The binding time was 300 s and the dissociation time was 300 s. When the assay was finished, data from which the response values of blank control had been deducted were fitted to a 1:1 Langmuir binding model using software, and then kinetic constants for antigen-antibody binding were calculated.

The response curves of hzF2-TGF-β RIIm2 and the control protein M7824 to the recombinant human PD-L1 protein are shown in FIG. 10 and FIG. 11, and the response curves of them to the recombinant human TGF-β 1 protein are shown in FIG. 12 and FIG. 13. The curves were fitted and affinities were calculated. The results showed that hzF2-TGF-β RIIm2 exhibited an affinity to PD-L1 with a KD of 1.58E-09 M and an affinity to TGF-β 1 with a KD of 2.46E-09 M; and M7824 exhibited an affinity to PD-L1 with a KD of 3.21E-09 M and an affinity to TGF-β 1 with a KD of 2.81E-09 M. The kinetic parameters in detailed are provided in Table 6 below. The results showed that hzF2-TGF-β RIIm2 had high affinity to both human PD-L1 and TGF-β 1.

TABLE 6

Detection results of affinity of the fusion protein hzF2-TGF-β RIIm2

| | PD-L1 | | | TGF-β1 | | |
|---|---|---|---|---|---|---|
| | KD (M) | kon(1/Ms) | kdis(1/s) | KD (M) | kon(1/Ms) | kdis(1/s) |
| hzF2-TGF-β RIIm2 | 1.58E−09 | 4.35E+05 | 6.87E−04 | 2.46E−09 | 1.15E+05 | 2.83E−04 |
| M7824 | 3.21E−09 | 2.05E+05 | 6.59E−04 | 2.81E−09 | 1.19E+05 | 3.33E−04 |

Example 9: Binding Activity of the Fusion Protein hzF2-TGF-β RIIm2 Detected by ELISA Plates were coated with recombinant human PD-L1-his protein (Accession No.: NP_054861.2, 19 aa-238 aa), human TGF-β 1 (Cat: CA59, Novoprotein Scientific Inc.), human TGF-β 2 (Cat: CJ79, Novoprotein Scientific Inc.), and human TGF-β 3 (Cat: CJ44, Novoprotein Scientific Inc.) respectively overnight at 4° C., each protein having a concentration of 1 μg/ml. Afterwards, the plates were blocked with 5% BSA in a constant temperature incubator at 37° C. for 60 min. HzF2-TGF-β RIIm2 and the control protein M7824 as well as an isotype control NC-hIgG1 (dilutions of 12 concentrations obtained through 3-fold serially diluting from an initial concentration of 10 μg/ml) were added into the plates which were then incubated in a constant temperature incubator at 37° C. for 60 min, then the plates were washed 4 times with PBST. 1:5000 dilution of HRP-anti-human Fc (Cat.: 109-035-098, Jackson ImmunoResearch) was added into the plates for incubation for 45 min, and then the plates were washed with PBST 4 times. TMB substrate (Cat: ME142, GalaxyBio, Beijing) was added for color development for 15 min. 2 M HCl was added to stop reaction; and absorbances of the plates at 450 nm were read and recorded.

The results showed that hzF2-TGF-β RIIm2 had binding activities to human PD-L1, TGF-β 1, TGF-β 2 and TGF-β 3, which were comparable to those of M7824: the half-maximal effective concentration (EC50) values were 0.261 nM, 0.394 nM, 18.045 nM and 1.121 nM respectively, while M7824 had half-maximal effective concentration (EC50) values of 0.209 nM, 0.472 nM, 18.172 nM and 0.981 nM respectively for human PD-L1, TGF-β 1, TGF-β 2 and TGF-β 3 (FIG. 14 to FIG. 17).

Example 10: Binding Activity of the Fusion Protein hzF2-TGF-β RIIm2 Detected by FACS Human breast cancer cells MDA-MB-231 naturally expressing human PD-L1 were added into 96-well plates at $2\times10^4$ cells/well, and then were blocked with added 5% BSA at room temperature for 30 min. Afterwards, hzF2-TGF-β RIIm2 and the control protein M7824 as well as an isotype control NC-hIgG1 (dilutions of 12 concentrations obtained through 3-fold serially diluting from an initial concentration of 10 nM), were added into the plates which were then incubated on ice for 1 h. The cells were washed with ice-cold PBS (containing 0.05% Tween) 2 times, and then 1:200 dilution of Goat Anti human IgG Fc-FITC (Cat: F9512, Sigma) was added into the plates which were then incubated on ice for 45 min. Then the cells were washed with ice-cold PBS (containing 0.05% Tween) 2 times and then resuspended in 200 μL PBS. Mean Fluorescence Intensity (MFI) values were measured by a flow cytometer.

The results showed that the half-maximal effective concentration (EC50) values of hzF2-TGF-β RIIm2 and M7824 in binding PD-L1 on the cell surface were 0.0717 nM and 0.197 nM, respectively (FIG. 18).

Example 11: Blocking Activity of the Fusion Protein hzF2-TGF-β RIIm2 Detected by ELISA Plates were coated with recombinant human PD-1-hFc protein (Accession No.: NP_005009.2, 21 aa-167 aa) overnight at 4° C., the protein having a concentration of 1 μg/ml. Afterwards, the plates were blocked with 5% BSA in a constant temperature incubator at 37° C. for 60 min. 50 μl of hzF2-TGF-β RIIm2 and the control protein M7824 as well as an isotype control NC-hIgG1 (dilutions of 12 concentrations obtained through 1.5-fold serially diluting from an initial concentration of 60 nM) were added into the plates, followed by the addition of 50 μL of PD-L1-mFc (Accession No.: NP_054862.1, 19 aa-238 aa) at a concentration of 1 μg/ml. The plates were then incubated in a constant temperature incubator at 37° C. for 60 min, and then were washed 4 times with PBST. 1:5000 dilution of HRP-anti-mouse Fc (Cat.: 115-035-071, Jackson ImmunoResearch) was added into the plates for incubation for 45 min, and then the plates were washed with PBST 4 times. TMB substrate (Cat: ME142, GalaxyBio, Beijing) was added for color development for 15 min. 2 M HCl was added to stop reaction; and absorbances of the plates at 450 nm were read and recorded.

The results showed that hzF2-TGF-β RIIm2 could effectively block the binding of the recombinant human PD-L1 to its receptor PD-1. The competitive inhibition effects of hzF2m9-TGF-β RIIm2 and M7824 on the binding of human PD-L1 to its receptor PD-1 were detected by ELISA, and the half-maximal inhibitory concentration (IC50) values of them were 7.533 nM and 6.935 nM, respectively (FIG. 19).

Example 12: Observation of Cytological Activity of the Fusion Protein hzF2-TGF-β RIIm2 to Block the Binding of PD-L1 to its Receptor PD1

CHO cells recombinantly expressing human PD-L1 and anti-CD3-ScFv (CHO-PD-L1-CD3L, JIANGSU T-MAB BIOPHARMA CO., LTD.) were inoculated into 96-well plates (Cat: 3917, Corning) at 5000 cells/well and incubated overnight in a cell incubator, and then supernatants were discarded. HzF2-TGF-β RIIm2 and the control protein M7824 (dilutions of 8 concentrations obtained through 2.5-fold serially diluting from an initial concentration of 5 μg/ml) (25 μL/well) and 50 μL of a suspension ($1\times10^6$ cells/mL) of Jurkat cells recombinantly expressing human PD-1 and luciferase (Jurkat-PD1-NFAT, JIANGSU T-MAB BIOPHARMA CO., LTD.) were added into the plates which in turned were incubated in a cell incubator for 6 h. Bio-Turbo firefly luciferase substrate (Cat: RA-GL03, RHINOZYME BIOTECHNOLOGY) was added to the plates at 125 μL/well, and the plates were placed in a microplate constant temperature oscillator and incubated at 800 rpm for 5 min in dark. A multifunctional microplate reader was set to operate under the Luminescence mode, with the Interpretation being 500 (a default value of the instrument). RLU values were read, and the detection results are shown in FIG. 20. As shown, hzF2-TGF-β RIIm2 and the control protein M7824 showed blocking effects on the PD-L1/PD1 pathway with EC50 values of 10.122 nM and 8.537 nM, respectively.

TABLE 7

Detection of biological activity of the fusion protein hzF2-TGF-β RIIm2

| No. | Name | $EC_{50}$ (nM) | Relative biological activity (%) |
|---|---|---|---|
| 1 | M7824 | 10.122 | N/A |
| 2 | hzF2-TGF-β RIIm2 | 8.537 | 119 |

Example 13: Evaluation of Antitumor Efficacy of the Fusion Protein hzF2-TGF-β RIIm2 in a Model of PBMC Immune Reconstitution Mice Subcutaneously Transplanted with Human Pharyngeal Squamous Cell Carcinoma Fadu Cells Human pharyngeal squamous carcinoma (FaDu) cells were inoculated subcutaneously in the right flank of 5-6 week old male NCG mice at a concentration of $5\times10^6$ cells/0.1 mL, and human PBMCs were inoculated into the mice at $2\times10^6$ cells/mouse. When the tumors grew to 40-60 $mm^3$, mice with tumor volume meeting the requirement were randomly grouped into 2 groups, 6 mice each group, and then were administered with hzF2-TGF-β RIIm2 and an isotype control hIgG1 respectively. The administration schedule is provided in Table 8. The results are shown in FIG. 21 and FIG. 22. As shown, hzF2-TGF-β RIIm2 significantly inhibited tumor growth and had a definite antitumor efficacy, achieving a tumor growth inhibition (TGI; Tumor weight) rate of 53%.

TABLE 8

Administration schedule for the subcutaneous transplantation model in PBMC immune reconstitution mice

| Group | Animals | Treatment | Dosage (mg/kg) | Administration route | Administration period |
|---|---|---|---|---|---|
| 1 | 6 | hzF2-TGF-β RIIm2 | 8 | i.p. | BIW × 5 |
| 2 | 6 | hIgG1 | 10 | i.p. | BIW × 5 |

Note:
the administration volume was 10 μl/g body weight, and the administration dosage can be adjusted when the body weight is reduced by 15-20%;
i.p.: intraperitoneal injection; BIW × 5: twice per week for 5 times in total.

Example 14: Evaluation of Antitumor Activity of the Fusion Protein hzF2-TGF-β RIIm2 in a Tumor Model of Human CD34+ Cord Blood Stem Cell Humanized Mice Subcutaneously Inoculated with HCC827 Cells Human non-small cell lung cancer HCC827 cell line was recovered and cultured, and cultured and passaged in RMPI 1640 medium (with addition of inactivated 10% FBS) in a 37° C., 5% $CO_2$ incubator. The tumor cells in logarithmic growth phase were used for in vivo tumor inoculation. 20 qualified female human CD34+ umbilical cord blood stem cell humanized mice, after 1 week of adaptive feeding, were inoculated with the human non-small cell lung cancer HCC827 cells and were observed for tumor volume and body weight after the inoculation of tumor cells. Mice with tumor volume between 120-200 $mm^3$ were selected and randomly grouped into 3 groups according to their tumor volume and body weight, 5 mice each group. Administration was started on the day of grouping and the day the administration started was regarded as day 0. The administration schedule and grouping information are provided in Table 9. In the present experiment, the antitumor efficacy of equimolar amounts of the tested hzF2-TGF-β RIIm2 and a control drug Atezolizumab, each administered alone, was detected in the tumor model of human CD34+ cord blood stem cell humanized mice subcutaneously inoculated with HCC827 cells. The results showed (FIG. 23, and Table 10), when administered alone, both hzF2-TGF-β RIIm2 at 8 mg/kg and Atezolizumab at 10 mg/kg showed strong efficacy, and in the group administered with hzF2-TGF-β RIIm2, a tumor growth inhibition (TGI; tumor volume) rate reached above 80%, superior to when Atezolizumab was administered.

TABLE 9

Grouping and administration information

| Group | Animals | Tested drug | Dosage (mg/kg) | Administration route | Administration period |
|---|---|---|---|---|---|
| 1 | 6 | Isotype | 10 | i.p. | BIW |
| 2 | 5 | Atezolizumab | 10 | i.p. | BIW |
| 3 | 5 | hzF2-TGF-β RIIm2 | 8 | i.p. | BIW |

TABLE 10

Antitumor effect of the test drugs in a model of human CD34+ cord blood stem cell humanized mice subcutaneously inoculated with HCC827 cells

| Treatment | PG-D0 TV (mm3) | PG-D46 TV (mm3) | TGI (%) | ΔT/ΔC (%) | p vlaue |
|---|---|---|---|---|---|
| Isotype | 155.96 | 555.37 | — | — | — |
| Atezolizumab 10 mg/kg | 160.89 | 306.73 | 63.48% | 36.52% | 0.1586504 |
| hzF2-TGF-β RIIm2 8 mg/kg | 155.78 | 221.70 | 83.50% | 16.50% | 0.000377 |

The above description of the embodiments of the invention is not intended to limit the present invention, and those skilled in the art may make various changes and modifications to the present invention without departing from the spirit of the present invention, which should fall within the scope of the appended claims.

What is claimed is:

1. A TGF-β RII mutant, characterized in that the TGF-β RII mutant corresponds to a mutant of the extracellular domain of wild-type TGF-β RII as shown in SEQ ID NO. 6, wherein the TGF-β RII mutant differs from the extracellular domain of wild-type TGF-β RII as shown in SEQ ID NO. 6 by one or more mutations selected from the group consisting of Q6N, D12T, and G20T; wherein the numbering of the amino acid residues of the extracellular domain of wild-type TGF-β RII refers to SEQ ID NO. 6.

2. The TGF-β RII mutant according to claim 1, characterized in that the mutant is capable of binding to TGF-β, and the TGF-β includes TGF-β1, TGF-β2 and TGF-β3.

3. A fusion protein comprising two or more functional fragments, characterized in that at least one of the functional fragments has the TGF-β RII mutant according to claim 1.

4. The fusion protein according to claim 3, characterized in that the two or more functional fragments function independently from each other.

5. The fusion protein according to claim 3, characterized in that the functional fragments further include an antibody or antigen-binding portion thereof, a receptor or ligand-binding portion thereof, a cytokine or fragment thereof, a cytotoxin or variant thereof, a label or tracer.

6. The fusion protein according to claim 3, characterized in that the functional fragments specifically bind to a target selected from the group consisting of a target for tumor or cancer immunotherapy, a target for chronic infectious disease immunotherapy, and a target for autoimmune disease therapy.

7. A multifunctional active molecule having two or more functional activities, characterized in that at least one of the functional activities is a TGF-β binding activity which is conferred by a polypeptide fragment having the TGF-β RII mutant according to claim 1.

8. The multifunctional active molecule according to claim 7, characterized in that the functional activities further include an antigen binding activity, a ligand binding activity, a cytokine activity, a cytotoxicity, or a labeling activity.

9. An antibody-TGF-β RII conjugate molecule, characterized in that the antibody targets a target for tumor therapy, and the TGF-β RII has the TGF-β RII mutant according to claim 1.

10. The antibody-TGF-β RII conjugate molecule according to claim 9, characterized in that the antibody specifically targets epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, or STAT5.

11. The antibody-TGF-β RII conjugate molecule according to claim 9, characterized in that the antibody is a murine antibody, a chimeric antibody, a humanized antibody, an Fab antibody, an Fab' antibody, an F(ab')2 antibody, an Fv antibody, a scFv antibody, or a single-domain antibody.

12. The antibody-TGF-β RII conjugate molecule according to claim 9, characterized in that the antibody is an anti-human PD-L1 antibody or antigen-binding fragment thereof, wherein the anti-human PD-L1 antibody or antigen binding fragment thereof has CDR1 as shown in SEQ ID NO. 25, CDR2 as shown in SEQ ID NO. 26, and CDR3 as shown in SEQ ID NO. 27 in the heavy chain, and has CDR1 as shown in SEQ ID NO. 28, CDR2 as shown in SEQ ID NO. 29, and CDR3 as shown in SEQ ID NO. 30 in the light chain.

13. The antibody-TGF-β RII conjugate molecule according to claim 9, characterized in that the antibody is an anti-human PD-L1 single-domain antibody, wherein the amino acid sequence of the anti-human PD-L1 single-domain antibody is SEQ ID NO. 20.

14. The antibody-TGF-β RII conjugate molecule according to claim 12 or 13, characterized in that the TGF-β RII mutant is linked to the anti-human PD-L1 antibody via a linker peptide.

15. A composition comprising the TGF-β RII mutant according to claim 1, the fusion protein according to claim 5, the multifunctional active molecule according to claim 10, or the antibody-TGF-β RII conjugate molecule according to claim 13, and a pharmaceutically acceptable excipient.

16. The fusion protein according to claim 4, characterized in that adjacent functional fragments are optionally linked via a polypeptide linker (Linker).

17. The fusion protein according to claim 6, characterized in that the target includes epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, and STAT5.

18. The multifunctional active molecule according to claim 7, characterized in that the functional activities further include binding activities to the following molecules: epidermal growth factor receptor (EGFR), vascular endothelial growth factor receptor (VEGFR), platelet-derived growth factor receptor (PDGFR), fibroblast growth factor receptor (FGFR), insulin receptor (InsR), Bruton's tyrosine kinase (BTK), HER2, CTLA, CD20, CD52, CD30, CD33, CD133, PD-1, PD-L1, Src, Abl, phosphatidylinositol 3-kinase (PI3K), protein kinase B (PKB/Akt), rapamycin target protein (mTOR), serine threonine protein kinase Ras, mitogen activated protein kinase (MAPK), STAT1, STAT3, and STAT5.

19. The antibody-TGF-β RII conjugate molecule according to claim 10, characterized in that the antibody specifically targets EGFR, VEGFR, PDGFR, FGFR, HER2, CTLA, CD20, CD133, PD-1, or PD-L1.

20. The antibody-TGF-β RII conjugate molecule according to claim 14, characterized in that the linker peptide comprises $(G_4S)n$, in which n is an integer from 1 to 4.

* * * * *